(12) United States Patent
Epperly et al.

(10) Patent No.: US 11,931,086 B2
(45) Date of Patent: Mar. 19, 2024

(54) TELESCOPING BONE SCREW

(71) Applicant: Arthrex Trauma, Inc., Naples, FL (US)

(72) Inventors: Scott James Epperly, Torrance, CA (US); Kyle F Dickson, Bellaire, TX (US)

(73) Assignee: Arthrex Trauma, Inc., Naples, FL (US)

( * ) Notice: Subject to any disclaimer, the term of this patent is extended or adjusted under 35 U.S.C. 154(b) by 212 days.

(21) Appl. No.: 17/152,679

(22) Filed: Jan. 19, 2021

(65) Prior Publication Data

US 2021/0137575 A1     May 13, 2021

Related U.S. Application Data

(63) Continuation of application No. 14/285,216, filed on May 22, 2014, now Pat. No. 11,020,158, which is a continuation of application No. 13/368,060, filed on Feb. 7, 2012, now abandoned, which is a continuation-in-part of application No. 13/045,470, filed on Mar. 10, 2011, now Pat. No. 9,204,910.

(60) Provisional application No. 61/312,251, filed on Mar. 10, 2010.

(51) Int. Cl.
| | |
|---|---|
| *A61B 17/86* | (2006.01) |
| *A61B 17/72* | (2006.01) |
| *A61B 17/74* | (2006.01) |
| *A61B 17/84* | (2006.01) |
| *A61B 17/88* | (2006.01) |

(52) U.S. Cl.
CPC ...... *A61B 17/8625* (2013.01); *A61B 17/7225* (2013.01); *A61B 17/7233* (2013.01); *A61B 17/7266* (2013.01); *A61B 17/74* (2013.01); *A61B 17/744* (2013.01); *A61B 17/844* (2013.01); *A61B 17/8872* (2013.01); *A61B 17/8888* (2013.01); *A61B 2017/8655* (2013.01)

(58) Field of Classification Search
CPC . A61B 17/72; A61B 17/7208; A61B 17/7216; A61B 17/7225
USPC ...................................... 606/62–68, 300–321
See application file for complete search history.

(56) References Cited

U.S. PATENT DOCUMENTS

| | | | |
|---|---|---|---|
| 2,397,545 A | * | 4/1946 | Hardinge ............. A61B 17/746 606/68 |
| 2,801,631 A | | 8/1957 | John |
| 4,621,629 A | | 11/1986 | Koeneman |
| 4,622,959 A | | 11/1986 | Marcus |
| 4,641,640 A | | 2/1987 | Griggs |
| 4,940,467 A | | 7/1990 | Tronzo |
| 5,032,125 A | | 7/1991 | Durham et al. |
| 5,041,116 A | | 8/1991 | Wilson |

(Continued)

FOREIGN PATENT DOCUMENTS

DE           19723339         12/1998

*Primary Examiner* — Matthew J Lawson
(74) *Attorney, Agent, or Firm* — Carlson, Gaskey & Olds, P.C.

(57) ABSTRACT

A bone screw for treating a bone fracture having a detent assembly on a body portion thereof. The detent assembly operative to secure the body from movement relative to a bone nail. The detent assembly includes a detent member, for example, an annular member, movable between a first and second position. Positioning the annular member in the second position operates to secure the body of the bone screw from movement relative to the bone nail.

17 Claims, 28 Drawing Sheets

(56) References Cited

U.S. PATENT DOCUMENTS

| | | | |
|---|---|---|---|
| 5,122,133 A | 6/1992 | Evans | |
| 5,957,642 A * | 9/1999 | Pratt | F16B 33/00 |
| | | | 36/134 |
| 5,976,139 A | 11/1999 | Bramlet | |
| 6,645,209 B2 * | 11/2003 | Hall, IV | A61B 17/746 |
| | | | 606/281 |
| 6,951,561 B2 * | 10/2005 | Warren | A61B 17/683 |
| | | | 606/328 |
| 7,503,919 B2 | 3/2009 | Shaw | |
| 8,470,005 B1 * | 6/2013 | Powlan | A61B 17/746 |
| | | | 606/68 |
| 9,320,555 B2 * | 4/2016 | Probe | A61B 17/744 |
| 2002/0045900 A1 * | 4/2002 | Harder | A61B 17/744 |
| | | | 606/65 |
| 2002/0156473 A1 * | 10/2002 | Bramlet | A61B 17/744 |
| | | | 606/62 |
| 2005/0010224 A1 | 1/2005 | Watkins et al. | |
| 2007/0260248 A1 | 11/2007 | Tipimeni | |
| 2008/0255559 A1 | 10/2008 | Levden et al. | |
| 2009/0069813 A1 | 3/2009 | Von Hoffman et al. | |
| 2009/0254089 A1 | 10/2009 | Tipirneni et al. | |
| 2009/0264885 A1 * | 10/2009 | Grant | A61B 17/746 |
| | | | 606/65 |
| 2009/0326534 A1 * | 12/2009 | Yamazaki | A61B 17/744 |
| | | | 606/301 |
| 2010/0312245 A1 | 12/2010 | Tipirneini et al. | |

* cited by examiner

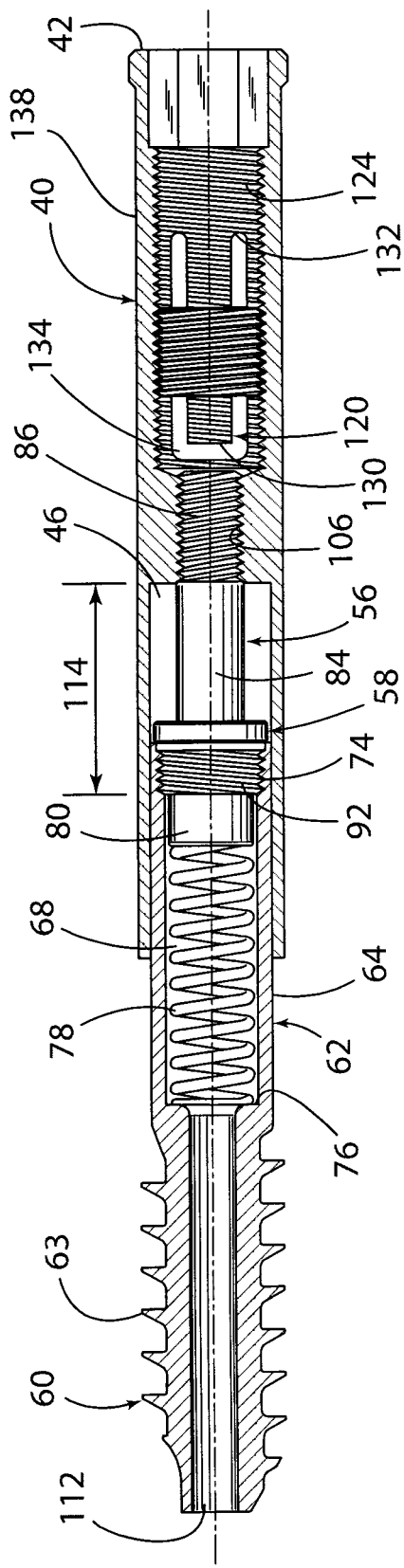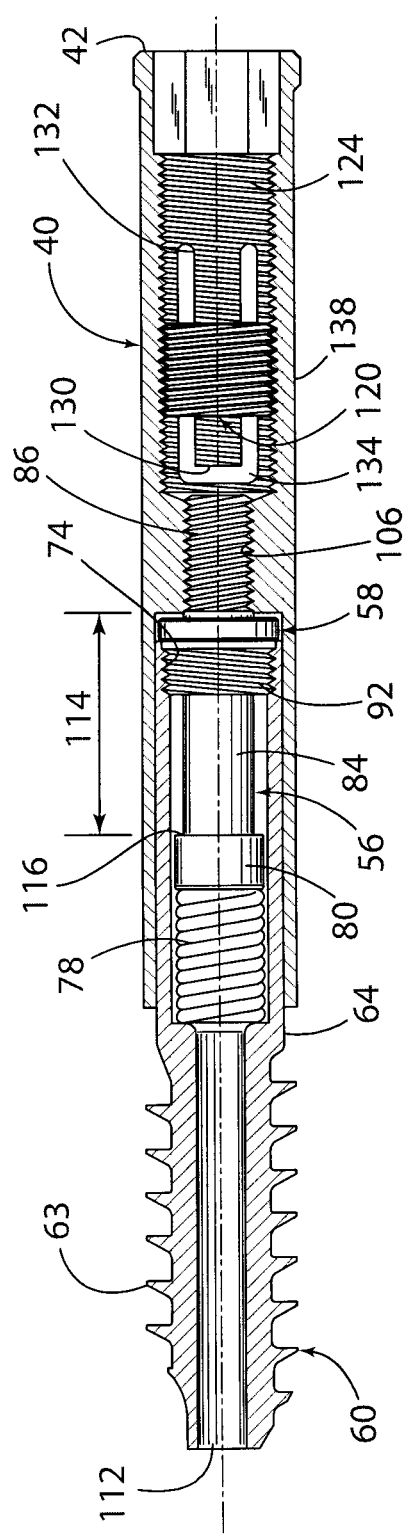
FIG. 6
FIG. 7

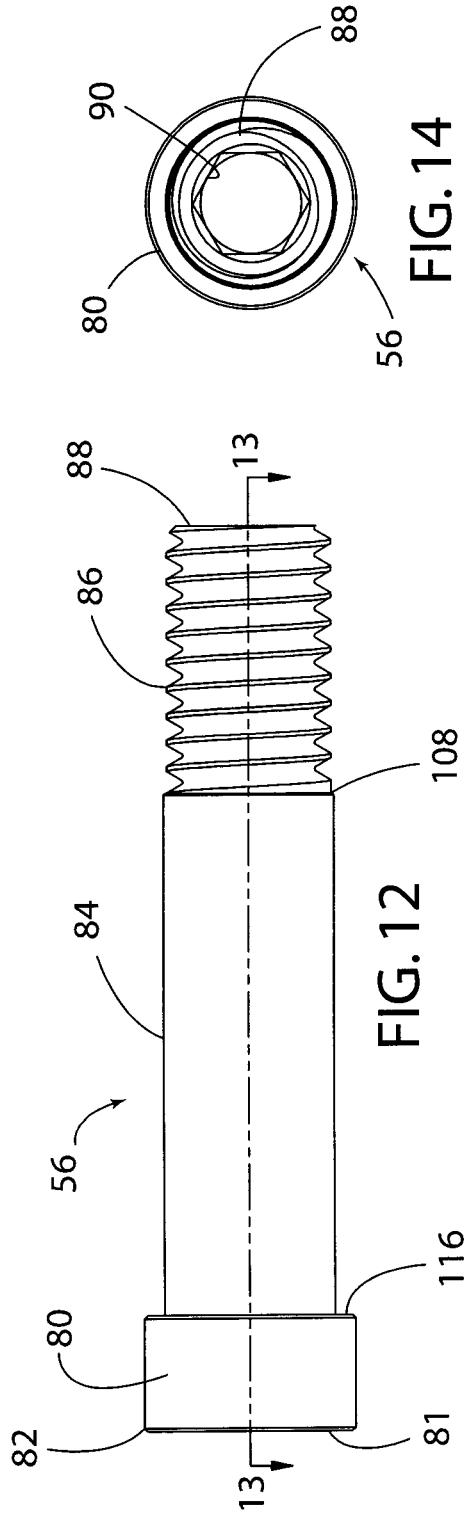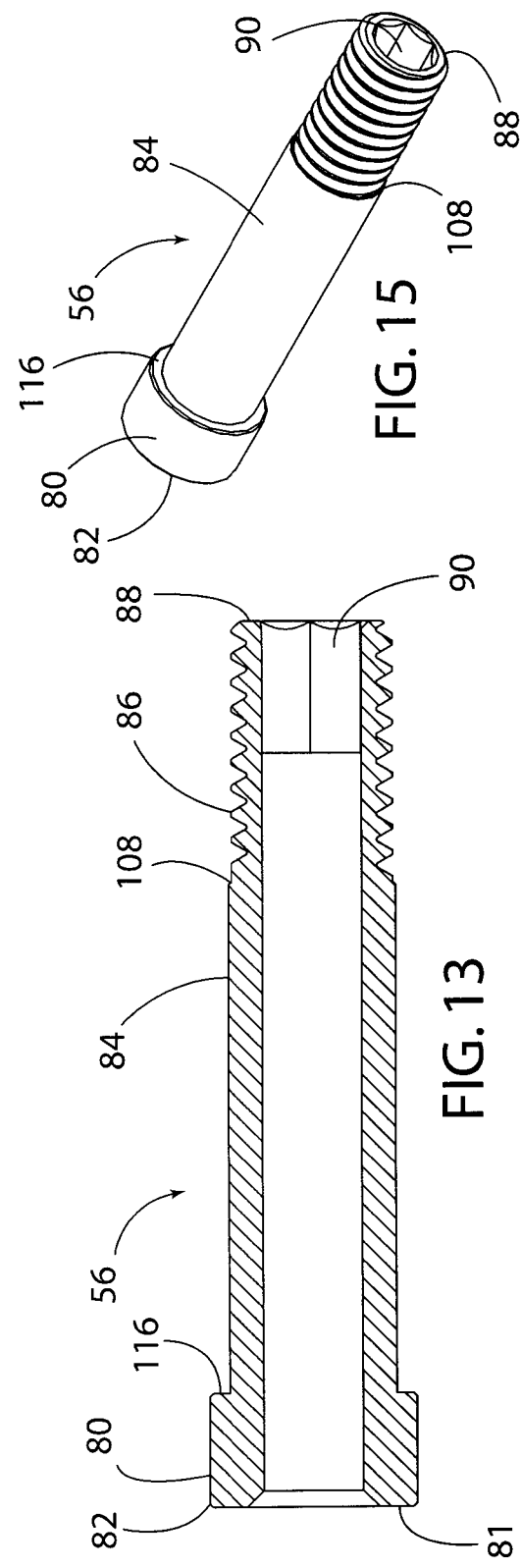

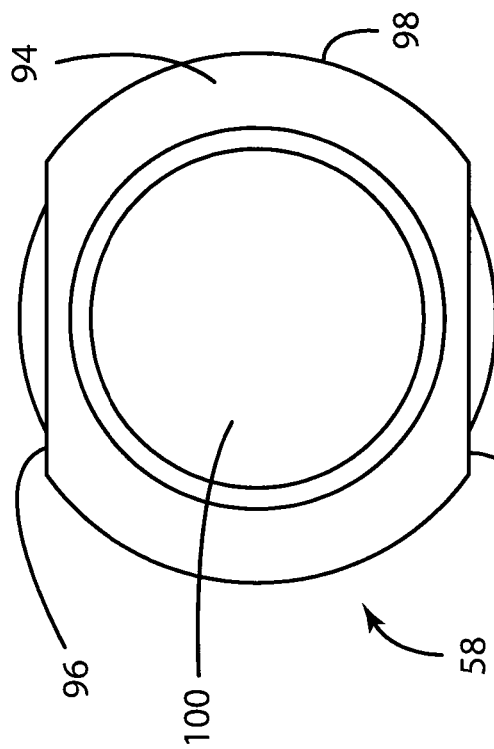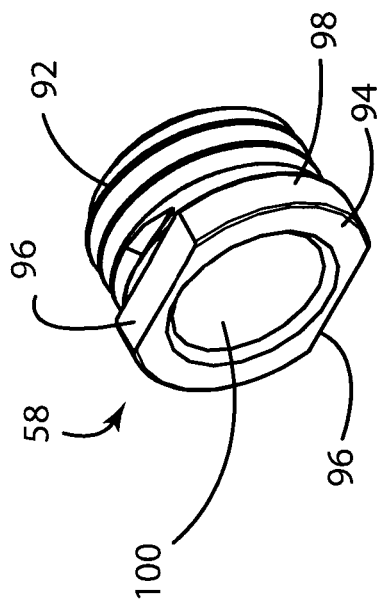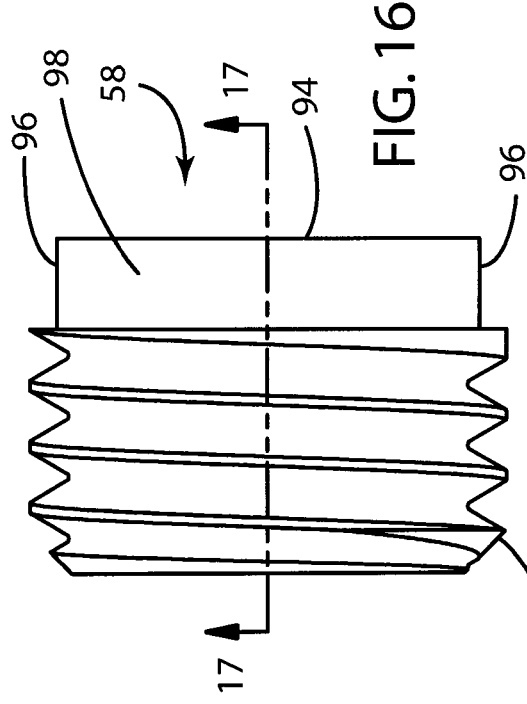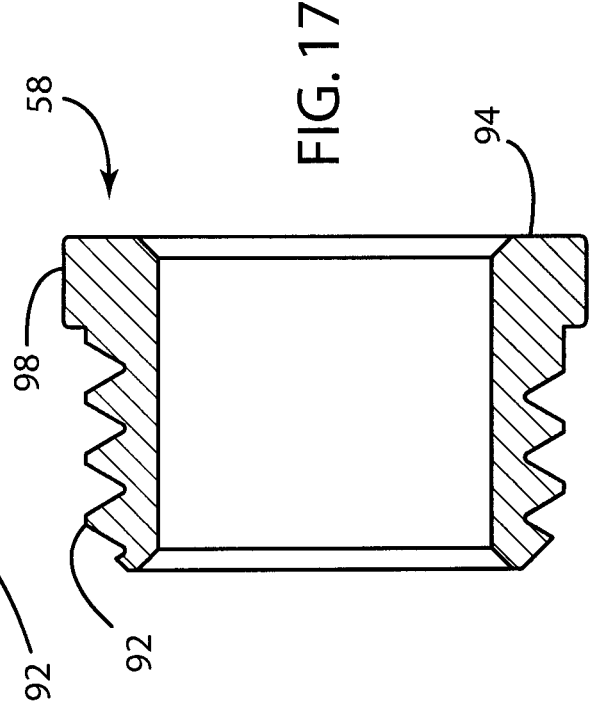

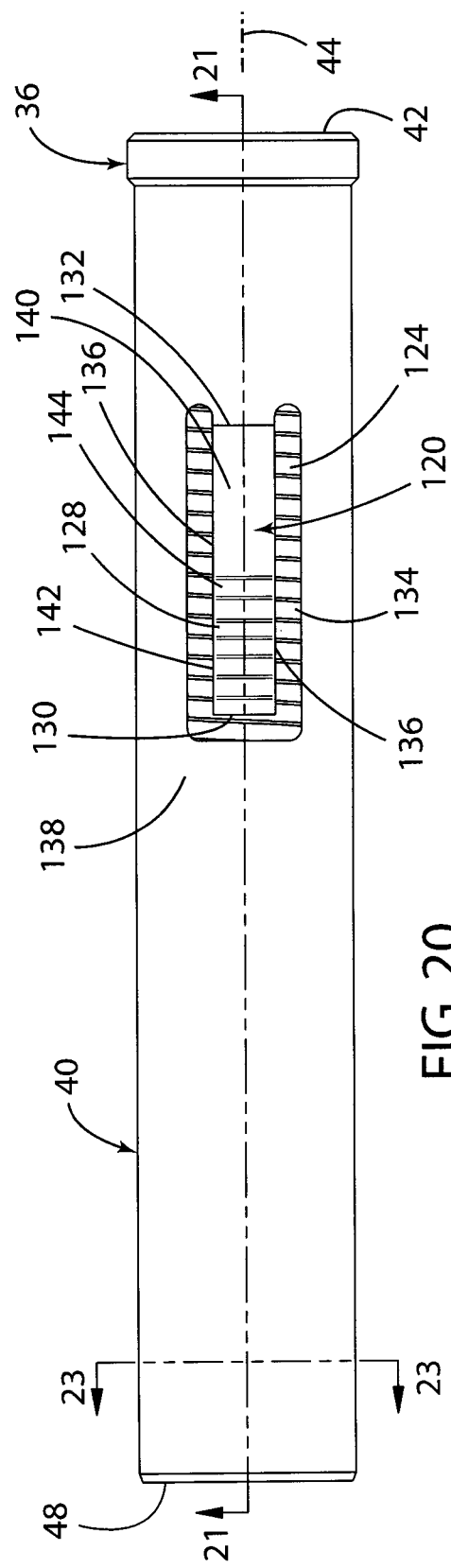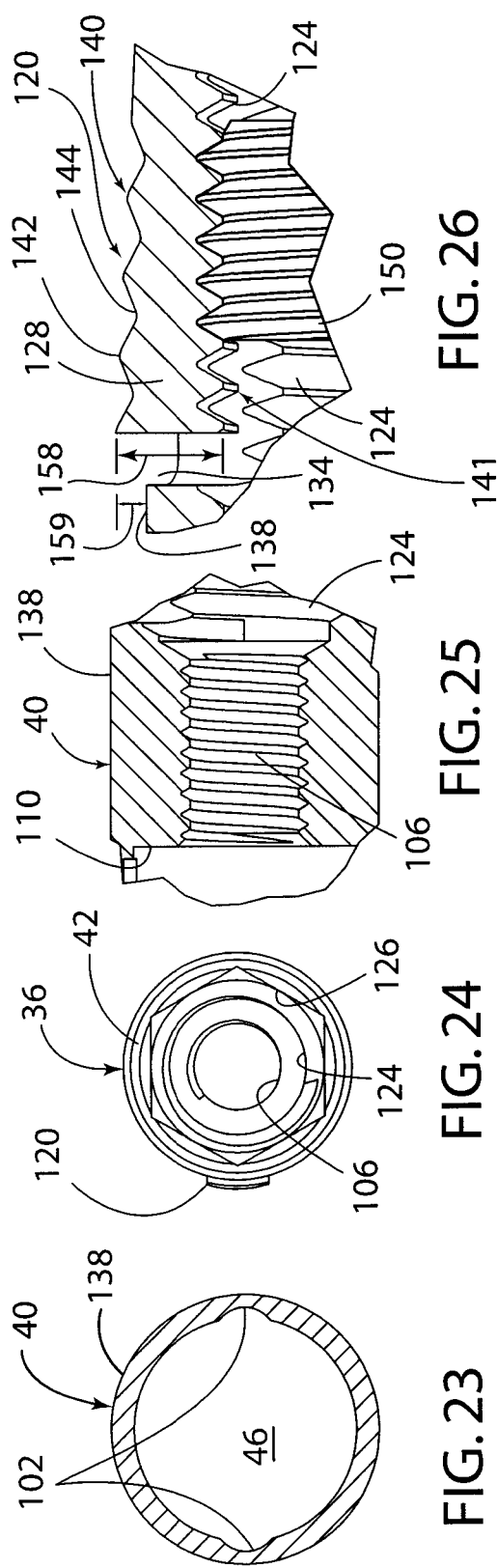

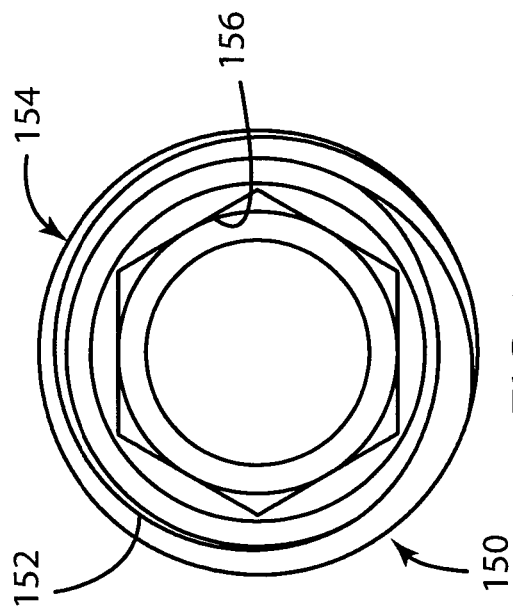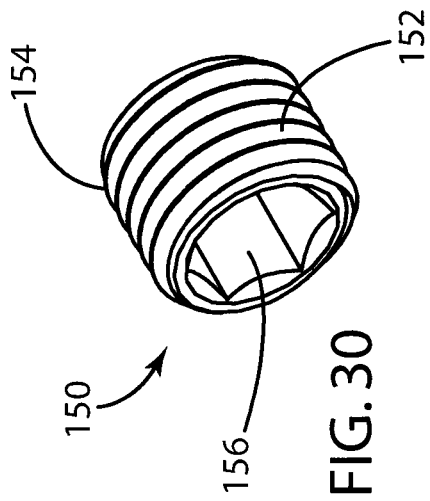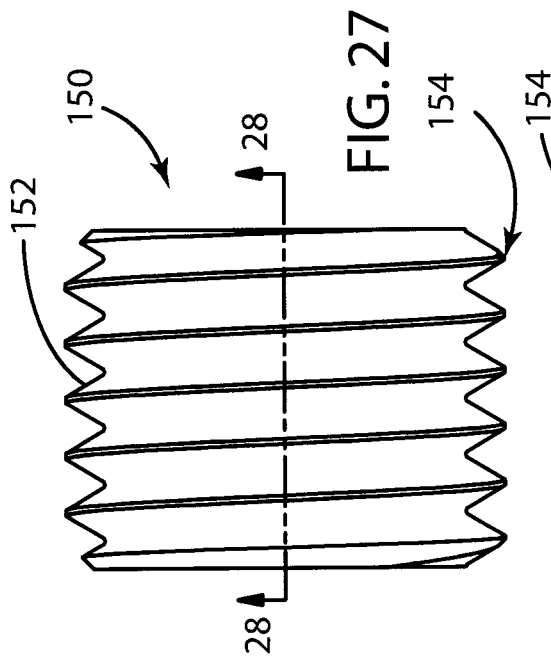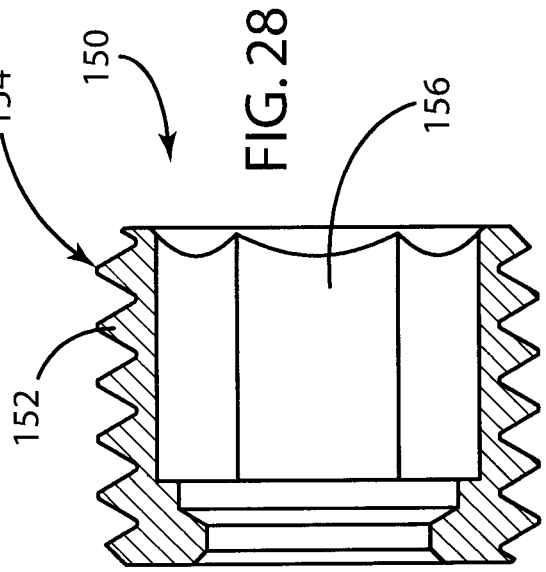

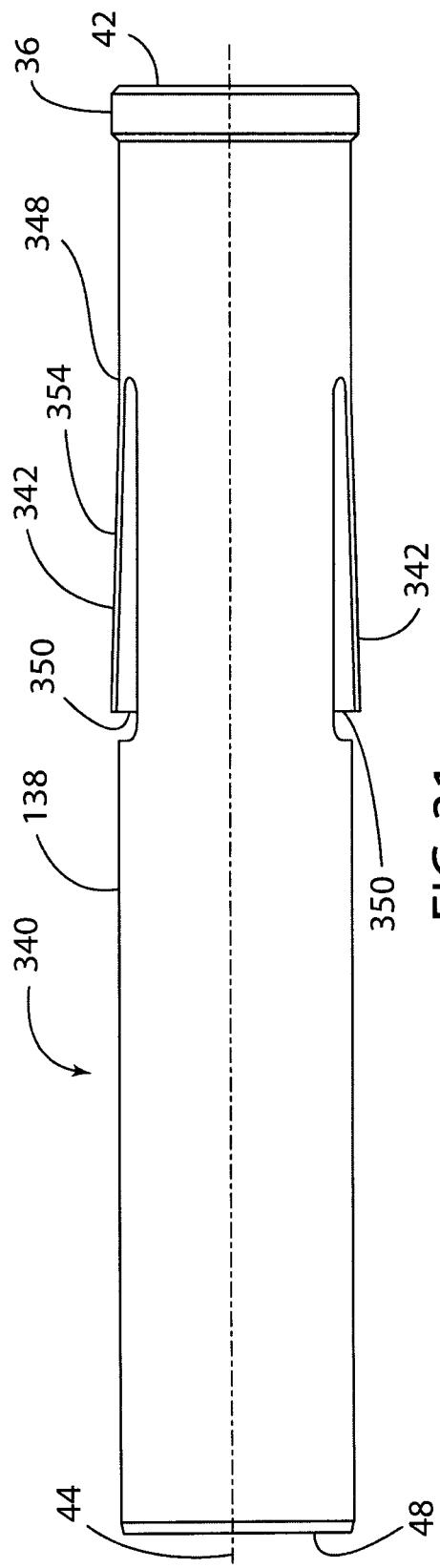
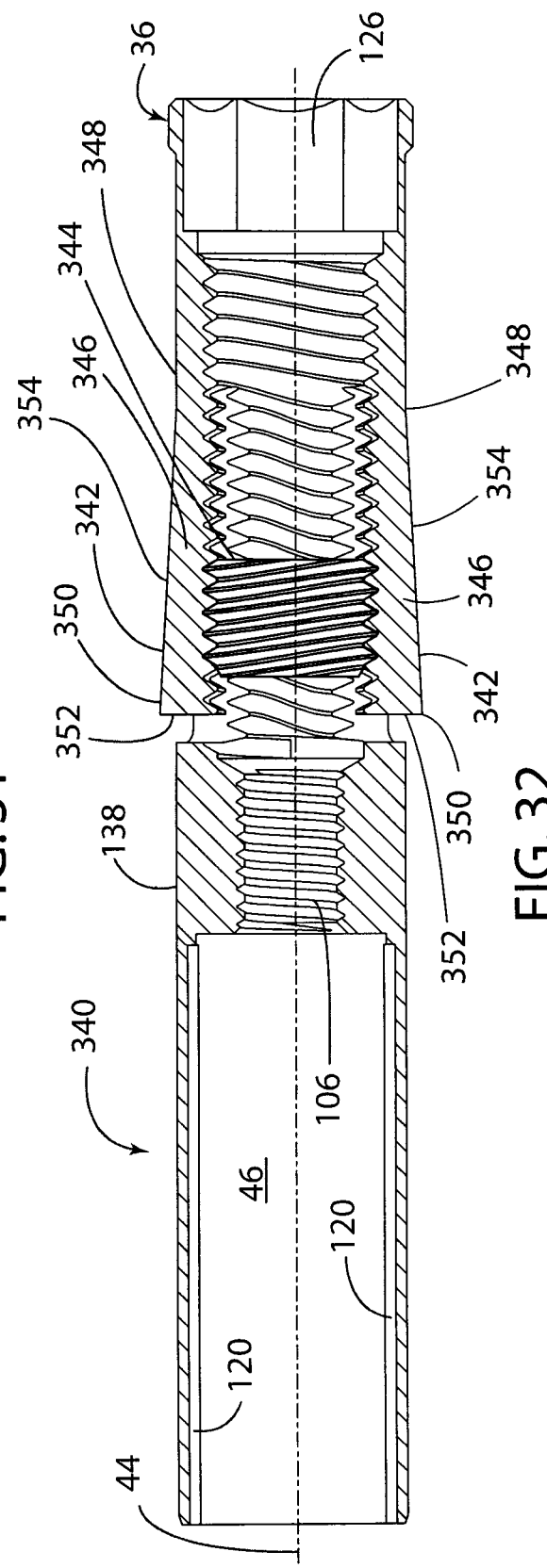
FIG. 31
FIG. 32

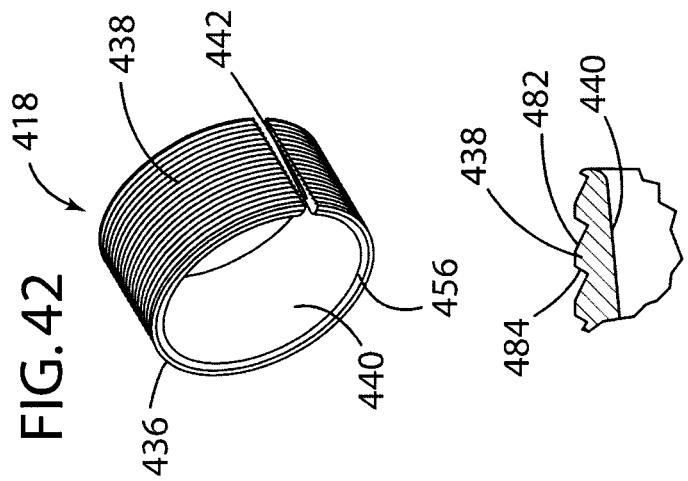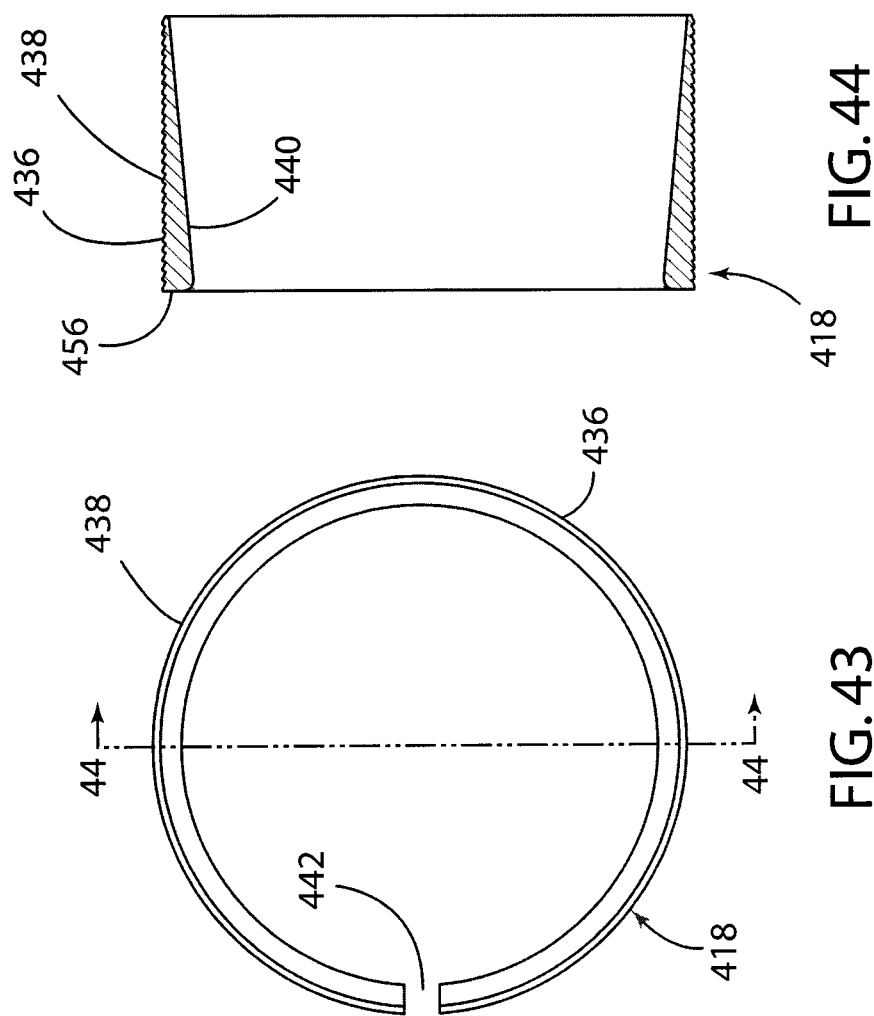

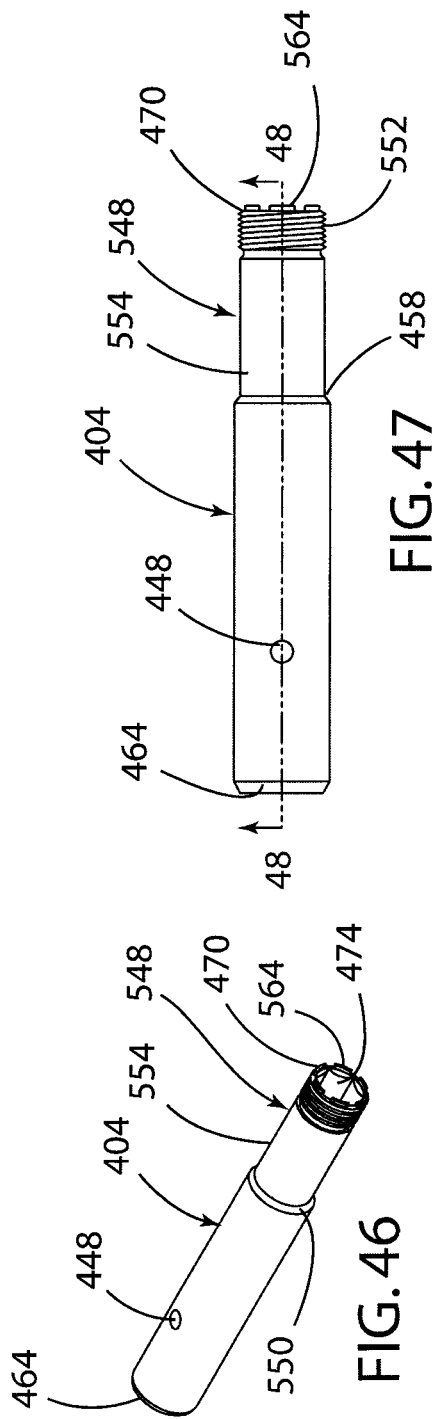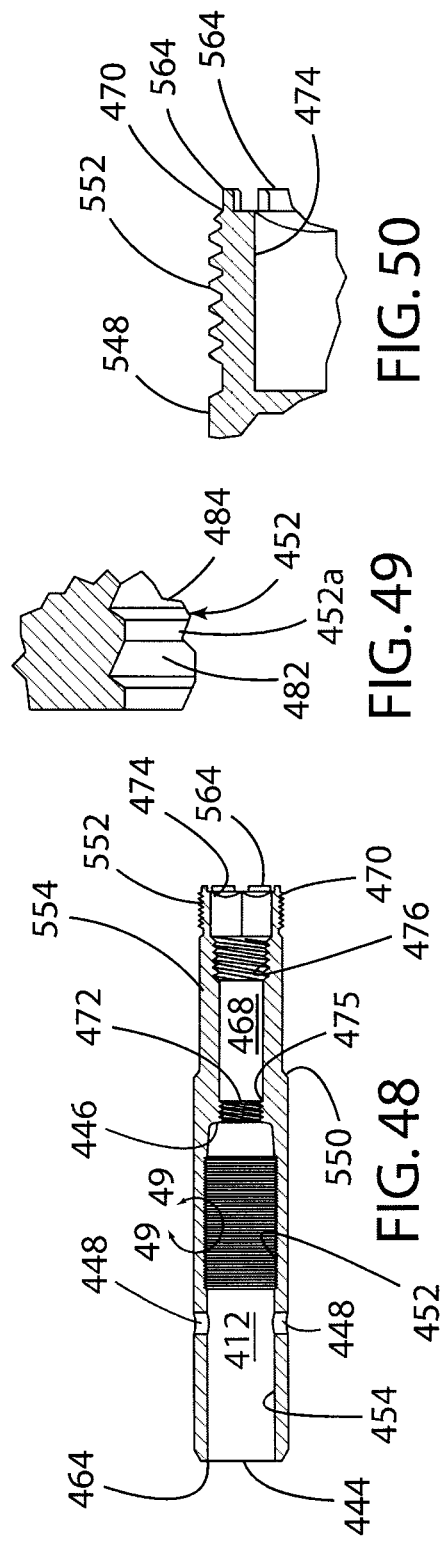

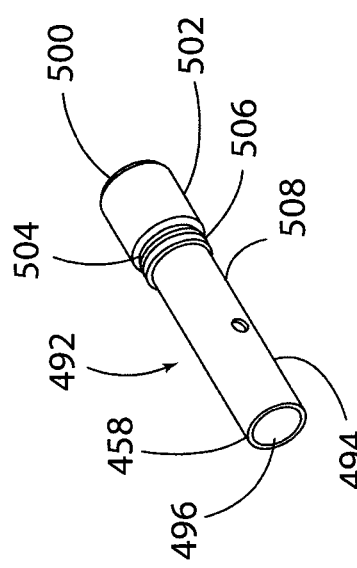
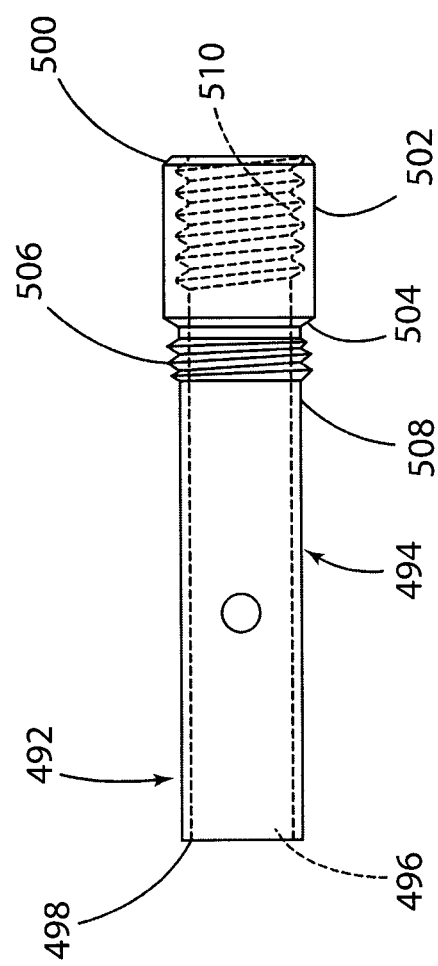

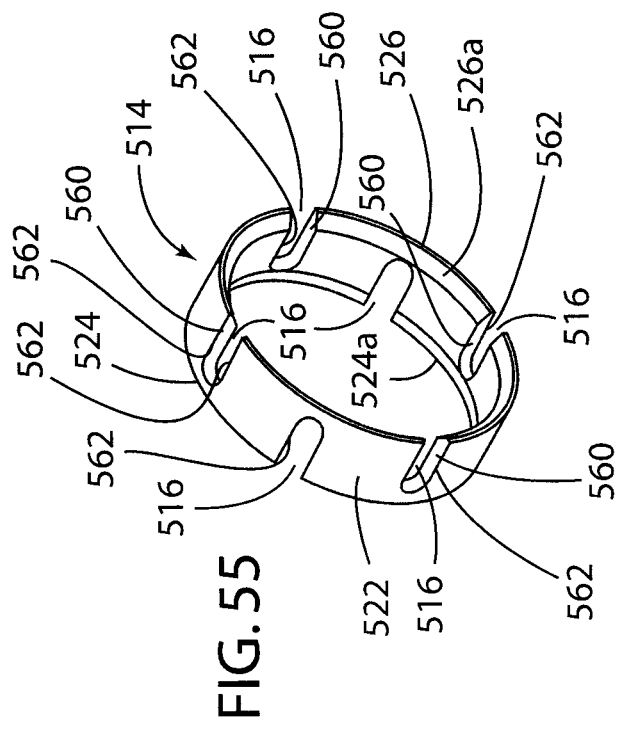
FIG.55
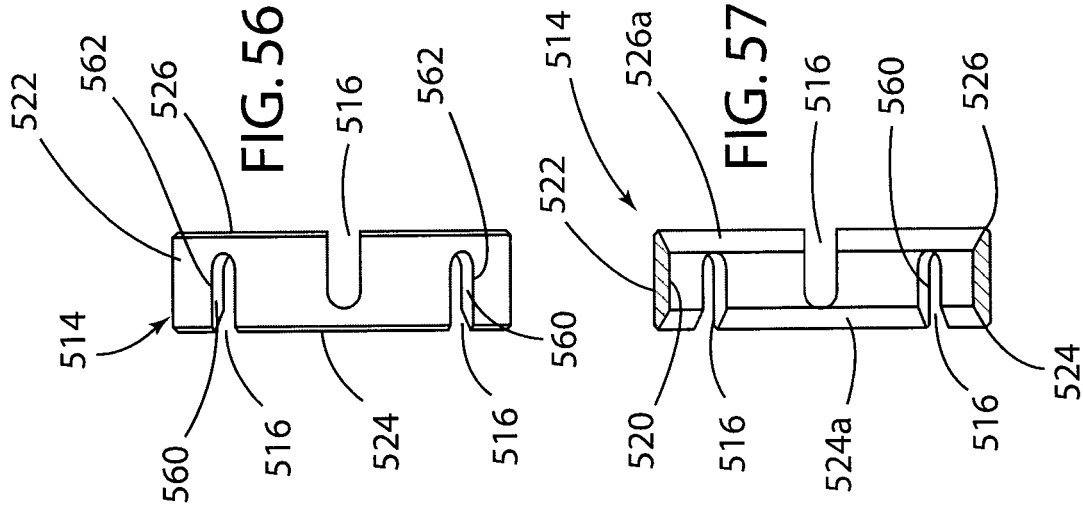
FIG.56
FIG.57

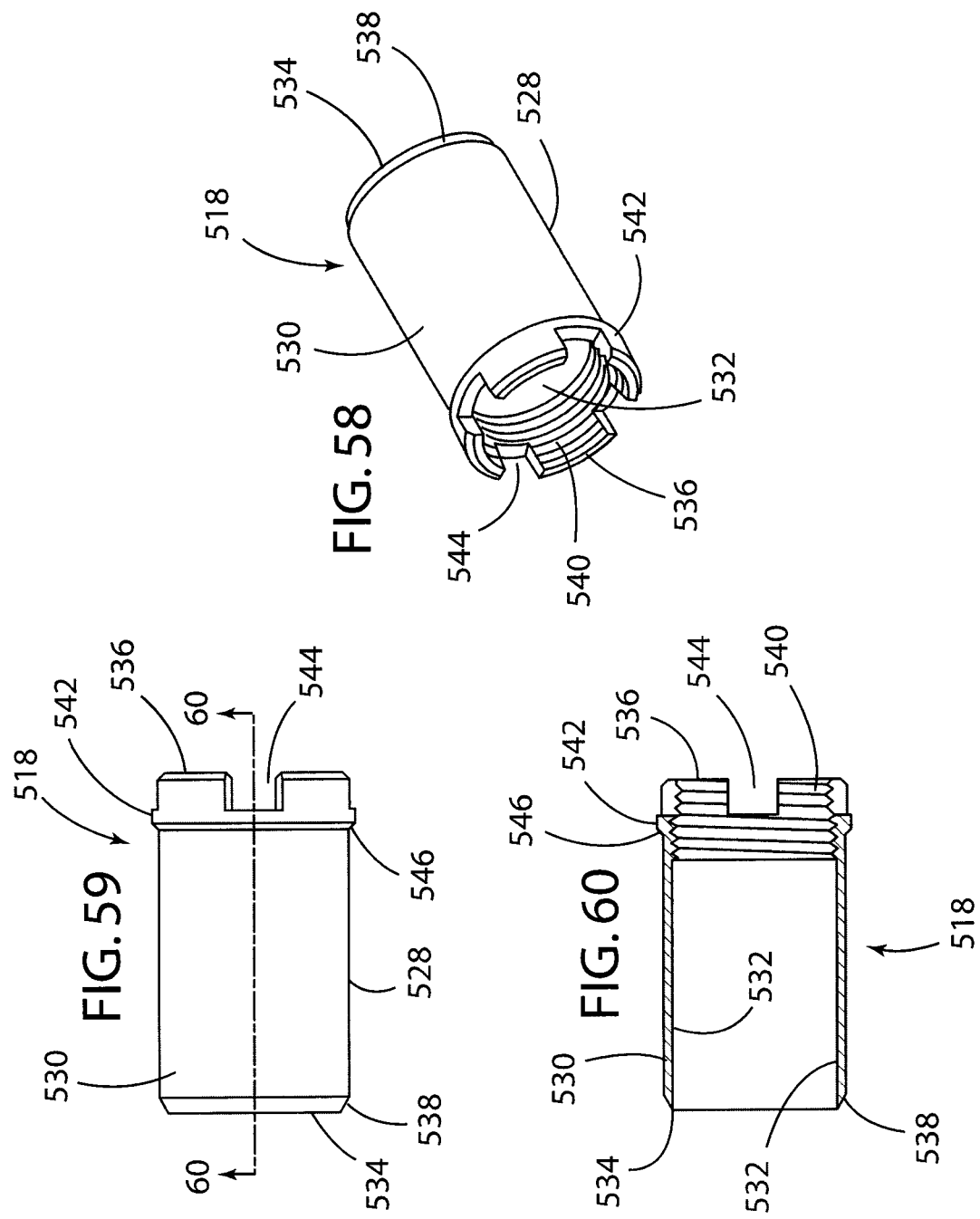

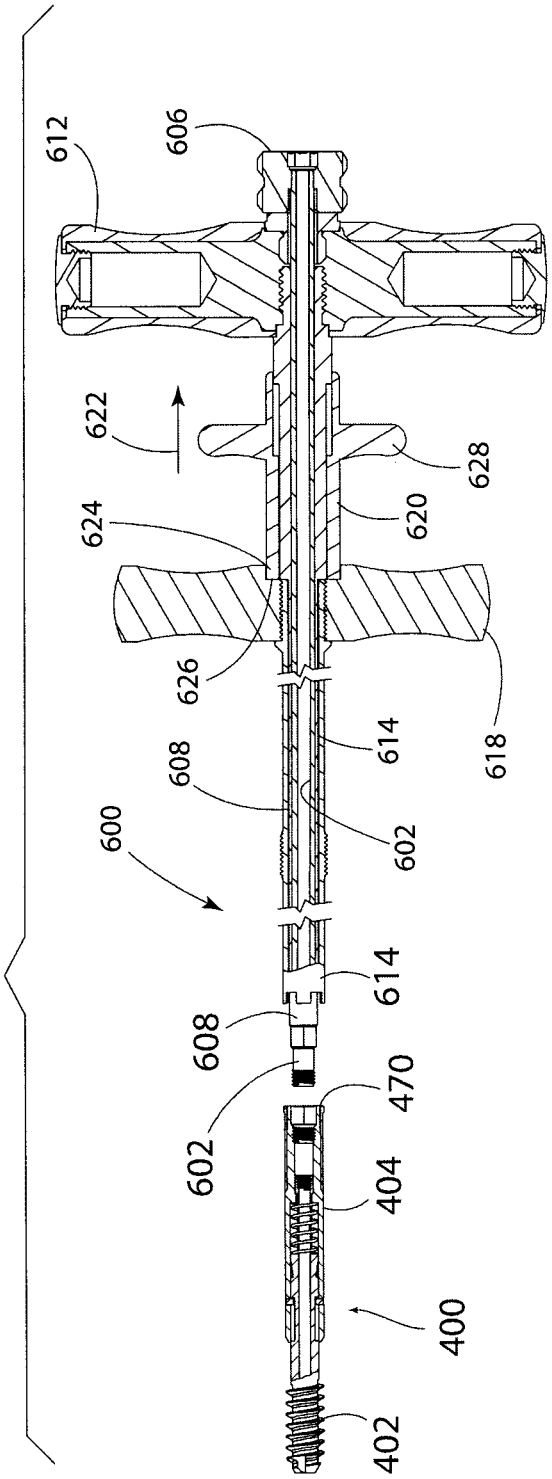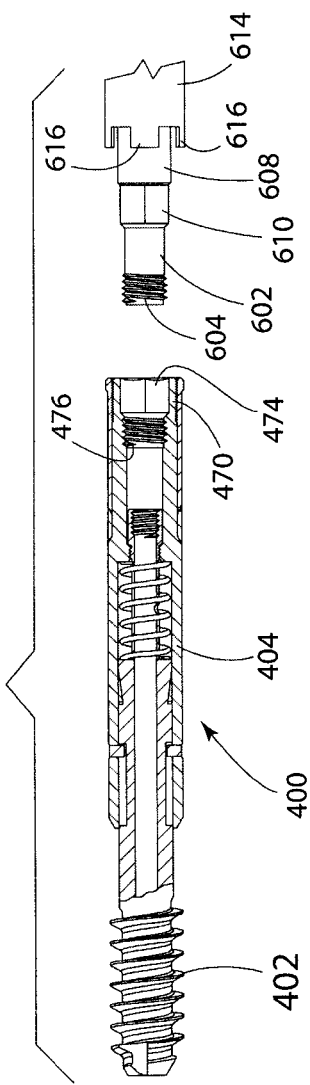
FIG.64
FIG.65

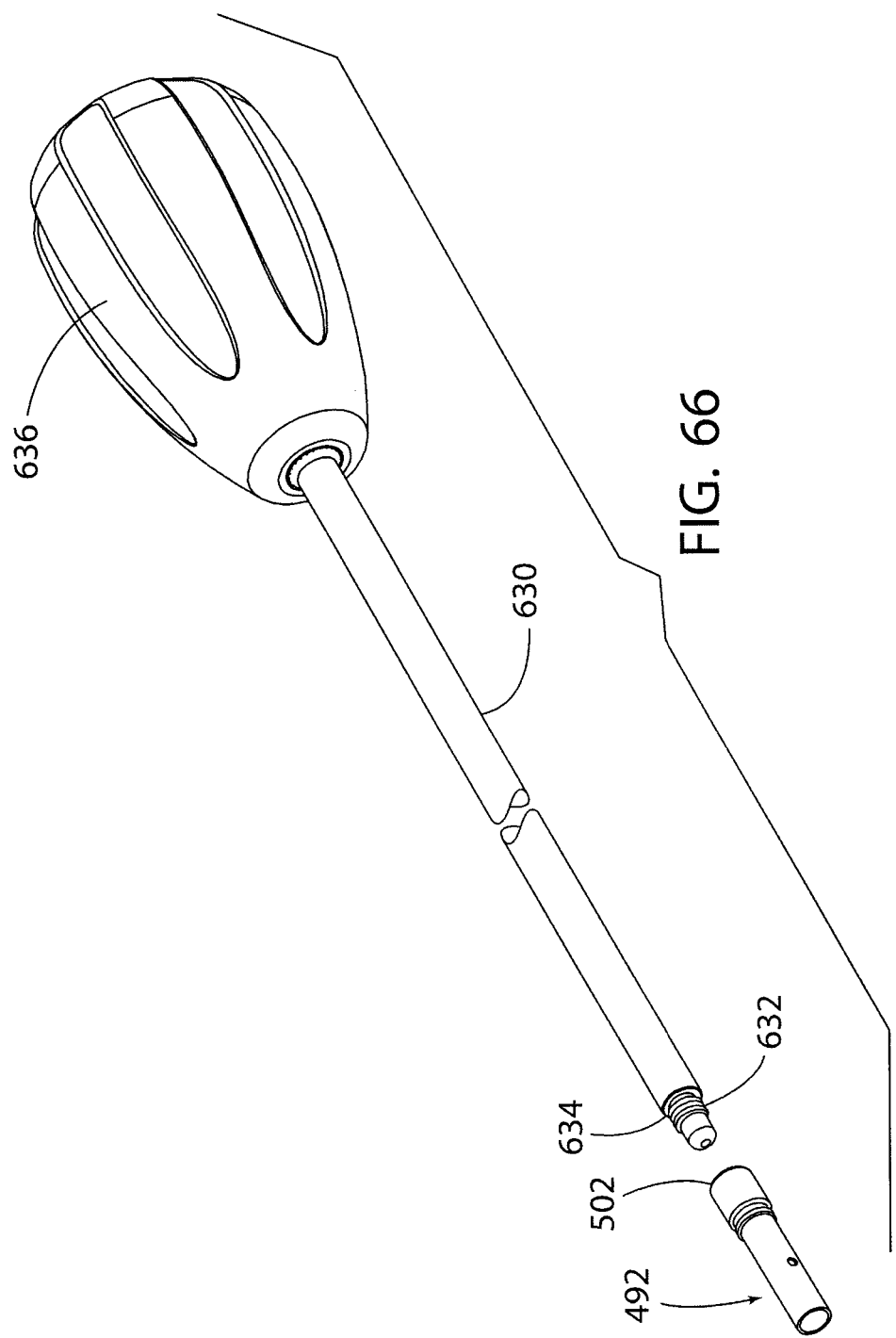

TELESCOPING BONE SCREW

CROSS-REFERENCE TO RELATED APPLICATIONS

This application is a continuation of U.S. patent application Ser. No. 14/285,216 filed May 22, 2014, currently pending, which is a continuation of U.S. patent application Ser. No. 13/368,060 filed on Feb. 7, 2012, now abandoned, which is a continuation-in-part of U.S. patent application Ser. No. 13/045,470 filed on Mar. 10, 2011, now U.S. Pat. No. 9,204,910, which claims the benefit of U.S. Provisional Application Ser. No. 61/312,251 filed Mar. 10, 2010, which is now expired.

STATEMENT REGARDING FEDERALLY SPONSORED RESEARCH OR DEVELOPMENT

Not Applicable.

BACKGROUND OF THE INVENTION

1. Field of the Invention

The present disclosure relates generally to bone treatment devices, and more particularly to a bone screw used to treat a bone fracture wherein the bone screw is suitable for treating fractures of the femur including trochanteric, intertrochanteric and femoral neck fractures.

2. Description of Related Art

Orthopedic fixation systems used for stabilizing a fracture often include an internal fixation device, typically an elongated implant such as a nail, screw or pin, inserted into the intramedullary canal of the bone to stabilize the fracture and promote healing. Such fixation systems are suitable for use in treating fractures of the neck, head, intertrochanter, sub-trochanteric, pathologic and certain ipsilateral shaft and neck fractures of the femur. The femur generally includes an elongated shaft, a ball shaped head that fits into the hip socket and a neck connecting the ball to the shaft. The shaft also includes a greater trochanter and a lesser trochanter.

For example, if the neck of the femur sustains a fracture a bone nail is inserted into the intramedullary canal and a bone screw inserted through an aperture in the head of the nail. The bone screw spans the fracture and threadably engages the femoral head. Typically, a smooth bore forms the aperture in the end of the nail. The bone screw extends through the smooth bore and rotates as it threadably engages the femoral head. Once the bone screw is suitably tightened, it is left in place during the healing process. In some instances, for example when the patient puts weight on the hip, the fracture will compress or settle. Thus, bone screw migration is one problem that may occur during the healing process. Specifically, when the patient puts weight on the hip the femoral head may move with respect to the femur; that is, the femoral head may slide medially or laterally at the fracture. The movement may be due to weakness in the bone, bone deterioration, misalignment of the fracture or other factors.

Depending upon the type of connection or engagement between the bone screw and the bone nail, movement of the femoral head with respect to the femur may result in "cut-out," that is the externally threaded end of the bone screw cuts or extends through the femoral head. Cut-out may occur when the bone screw is fixedly secured to the bone nail and does not move in the aperture. As the femoral head moves, due to settlement of the fracture or bone deterioration, it slides or travels along the bone screw. Eventually the femoral head moves close enough to the femur that the threaded end of the bone screw breaks through or pierces the femoral head and extends into the hip joint.

If the bone screw is slidably fixed in the aperture, that is the bone screw is constrained against rotation but is allowed to slide longitudinally in the smooth bore of the aperture, compression of the fracture may cause the head of the bone screw to extend outward significantly past the outer surface of the femur creating a raised surface that can cause pain at the hip joint. In addition, leaving the bone screw free to move with respect to the bone nail may cause the bone screw to migrate or loosen, thus creating a risk of failure at the fracture.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

SUMMARY OF THE INVENTION

An apparatus for repairing a bone fracture comprising a bone screw having a body. The body having a socket formed in one end thereof with a plunger assembly disposed in the socket. The body further includes a detent assembly, the detent assembly including a detent member operable to move between a first position and a second position wherein positioning the detent member in the second position secures the body whereby the plunger assembly includes a plunger portion that moves independent of the body.

The detent assembly further including a lock ring and a lock sleeve. The lock sleeve operative to act on the lock ring to move the lock ring from a first position to the second position. Wherein when the lock ring is in the second position, an outer surface of the lock ring is urged outward past an outer surface of the body.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features and advantages of the disclosure will become apparent from a consideration of the subsequent detailed description presented in connection with the accompanying drawings in which:

FIG. 6 is a cross-sectional side view of a bone screw according to the present invention with the plunger assembly extended;

FIG. 7 is a cross-sectional side view of a bone screw according to the present invention with the plunger assembly compressed;

FIG. 12 is a side view of a guide member for use with a bone screw according to the present invention;

FIG. 13 is a cross-sectional view of the guide member of FIG. 12 taken along line 13-13;

FIG. 14 is an end of view of the guide member of FIG. 12;

FIG. 15 is a perspective view of the guide member of FIG. 12;

FIG. 16 is a side view of a retainer for use with a bone screw according to the present invention;

FIG. 17 is a cross-sectional view of the retainer of FIG. 16 taken along line 17-17;

FIG. 18 is an end view of the retainer of FIG. 16;

FIG. 19 is a perspective view of the retainer of FIG. 16;

FIG. 20 is a side view of a body for use with a bone screw according to the present invention;

FIG. 23 is cross-sectional view of one end of the body of FIG. 22 taken along the lines 23-23;

FIG. 24 is an end view of the body of FIG. 22;

FIG. 25 is an enlarged cross-sectional area taken within the circle 25 of FIG. 22;

FIG. 26 is an enlarged cross-sectional area taken within the circle 26 of FIG. 22;

FIG. 27 is a side view of a set screw for use with a bone screw according to the present invention;

FIG. 28 is a cross-sectional view taken along lines 28-28 of FIG. 27;

FIG. 29 is an end view of the set screw of FIG. 27;

FIG. 30 is a perspective view of the set screw of FIG. 27;

FIG. 31 is a side view of an alternative embodiment of a body for use with a bone screw according to the present invention;

FIG. 32 is a cross-sectional view of the body of FIG. 31;

FIG. 42 is a perspective view of an annular wedge for use with a bone screw according to one embodiment of the present invention;

FIG. 43 is an end view of the annular wedge of FIG. 42;

FIG. 44 is a cross-sectional side view of the annular wedge of FIG. 43 taken along line 44-44;

FIG. 45 is an enlarged side view of a portion of the annular wedge of FIG. 42;

FIG. 46 is a perspective view of a body for use with a bone screw according to one embodiment of the present invention;

FIG. 47 is a top view of the body of FIG. 46

FIG. 48 is a cross-sectional side view of the body of FIG. 46;

FIG. 49 is an enlarged partial cross-sectional side view of the body of FIG. 46 taken in circle 49-49;

FIG. 50 is an enlarged cross-sectional side view of one end of the body of FIG. 46;

FIG. 53 is a perspective view of a lockout tube according to one embodiment of the present invention;

FIG. 54 is a side view of the lock out tube of FIG. 53;

FIG. 55 is a perspective view of a clock ring according to one embodiment of the present invention;

FIG. 56 is a side view of the lock ring of FIG. 55;

FIG. 57 is a cross-sectional side view of the lock ring of FIG. 55;

FIG. 58 is a perspective view of a lock sleeve according to one embodiment of the present invention;

FIG. 59 is a side view of the lock sleeve of FIG. 58;

FIG. 60 is a cross-sectional side view of the lock sleeve of FIG. 58;

FIG. 64 is a cross-sectional view of the installation equipment of FIG. 63 shown adjacent a bone screw according to the present invention;

FIG. 65 is an enlarged cross-sectional view of the installation equipment of FIG. 63; and FIG. 66 is a perspective view of a lockout tube removal tool for use in removing the lockout tube.

DETAILED DESCRIPTION OF THE PREFERRED EMBODIMENTS

Figures 1, 2:
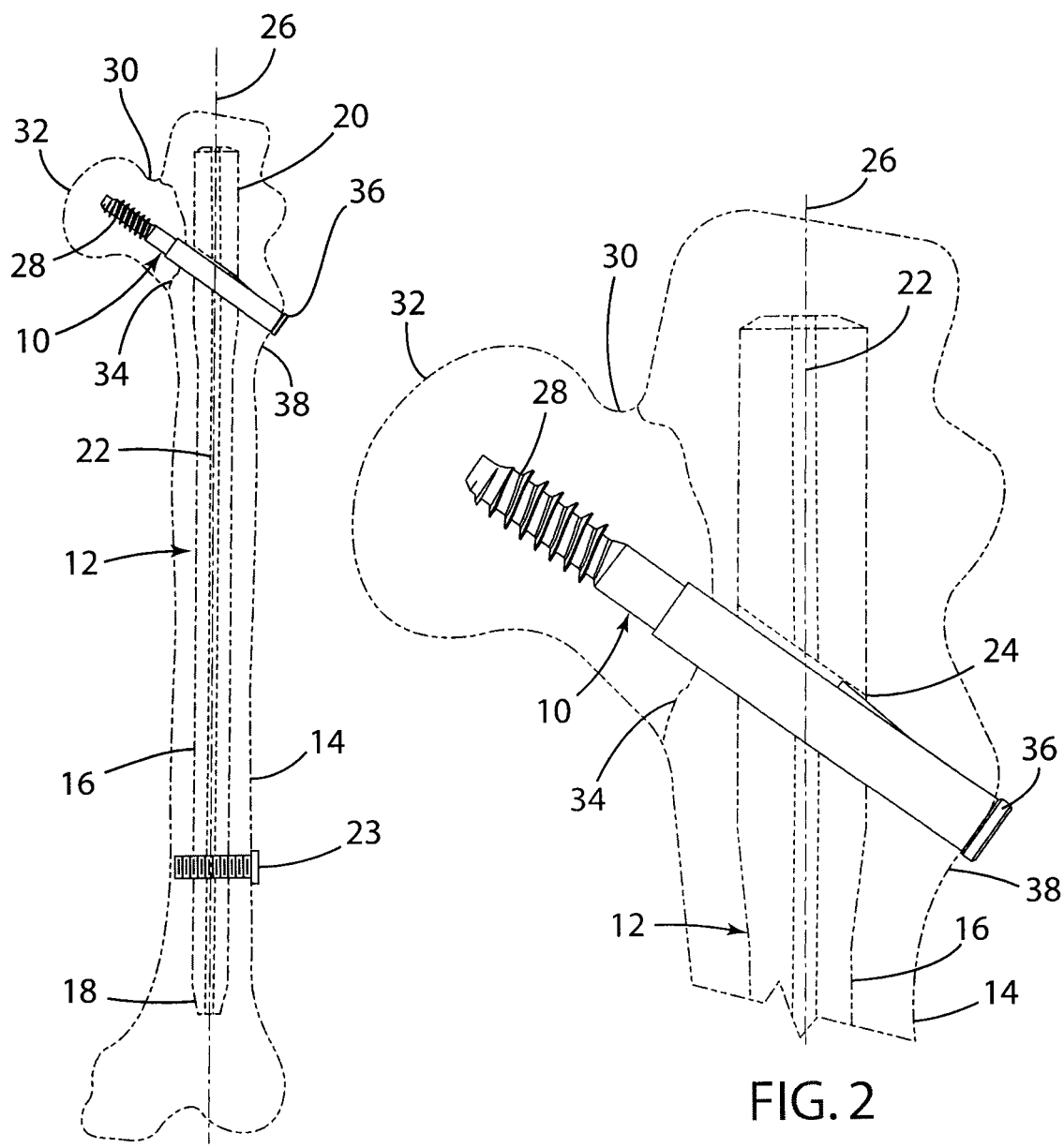
FIG. 1 is a schematic view of a bone screw according to one embodiment of the present invention shown as part of a fixation system placed in an assembled condition within a long bone such as a femur.
FIG. 2 is an enlarged schematic view of a bone screw according to one embodiment of the present invention shown extending through the proximal end of a bone nail placed in a femur.

The following description of the preferred embodiment(s) is merely exemplary in nature and is in no way intended to limit the invention, its application, or uses.

For the purposes of promoting an understanding of these principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art having possession of this disclosure, are to be considered within the scope of the disclosure claimed.

Before the present apparatus and methods for treating a bone fracture are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a", "an", and "the" include plural referents unless the context clearly dictates otherwise. Moreover, as used herein, the terms "comprising", "including", "containing", "characterized by" and grammatical equivalents thereof are inclusive or open-ended terms that do not exclude additional, unrecited elements or method steps. In addition, the term "at" when referring to the location or placement of an element or object means in, near or by the area or location occupied by the particular structure or element referred to.

As used herein, the term "proximal" shall refer broadly to the concept of a nearest portion.

As used herein, the term "distal" shall generally refer to the opposite of proximal, and thus to the concept of a further portion, or a furthest portion, depending upon the context.

FIGS. 1-2 show a schematic view of a bone screw, seen generally at 10, according to the present invention as part of a fixation system, seen generally at 12. The fixation system 12, according to one embodiment, is shown placed in an assembled condition within a bone, illustrated here as a femur 14. The fixation system 12 includes a bone nail 16 having a distal end 18 and a proximal end 20. A passageway 22 extends longitudinally through the bone nail 16 between the proximal end 20 and the distal end 18. The passageway 22 receives insertion and extraction instrumentation, such as a guide wire (not shown), used to position the bone nail 16 within the femur 14. Typically, the distal end 18 of the bone nail 16 is inserted into the femur 14 first and follows the path of the guide wire. Whereby, the bone nail 16 is inserted into the intramedullary cavity of the femur 14. One or more distal anchoring members 23 may be used to anchor the distal end 18 of the bone nail 16 in place. It will be understood that the anchoring members 23 may be screws or any other suitable variety of fastening mechanism known in the art for use with trochanteric nails. Accordingly, the shape, size and configuration of the anchoring members 23 may vary within the scope of the present disclosure. The term "nail" as used here refers to a connective orthopedic nail implant, including but not limited to a trochanteric nail for use in a femur, as well as any other connective implant device suitable for use in any bone of interest.

The proximal end 20 of the bone nail 16 includes an aperture or throughbore 24 extending through the proximal end 20 in a direction typically angled with respect to the longitudinal axis 26 of the bone nail 16. The bone screw 10 extends through the aperture 24 such that a threaded portion 28 of the bone screw 10 extends through the femoral neck 30 of the femur 14 and is seated within the dense cortical bone of the femoral head 32. The bone screw 10 preferably extends parallel to the longitudinal axis of the femoral head 32 and femoral neck 30 when extending through the aperture 24. The bone screw 10 spans the fracture illustrated as the jagged line 34 in the drawings.

During installation the bone screw 10 is tightened or rotated until the head 36 of the bone screw 10 engages the outer cortex 38 of the femur 14 whereby continued tightening or rotating of the bone screw 10 creates a force that draws the femoral head 32 toward the femur 14 and compresses the fracture 34. It will be understood that the bone screw 10 may be useful in other types of bones, in addition to femurs, with or without the bone nail 16 in accordance with the principles of the present disclosure. Further, additional embodiments of the present invention may include using the bone screw 10 of the present invention with other types of side plates or supporting or reinforcing members used in orthopedic fixation systems.

Figure 3:
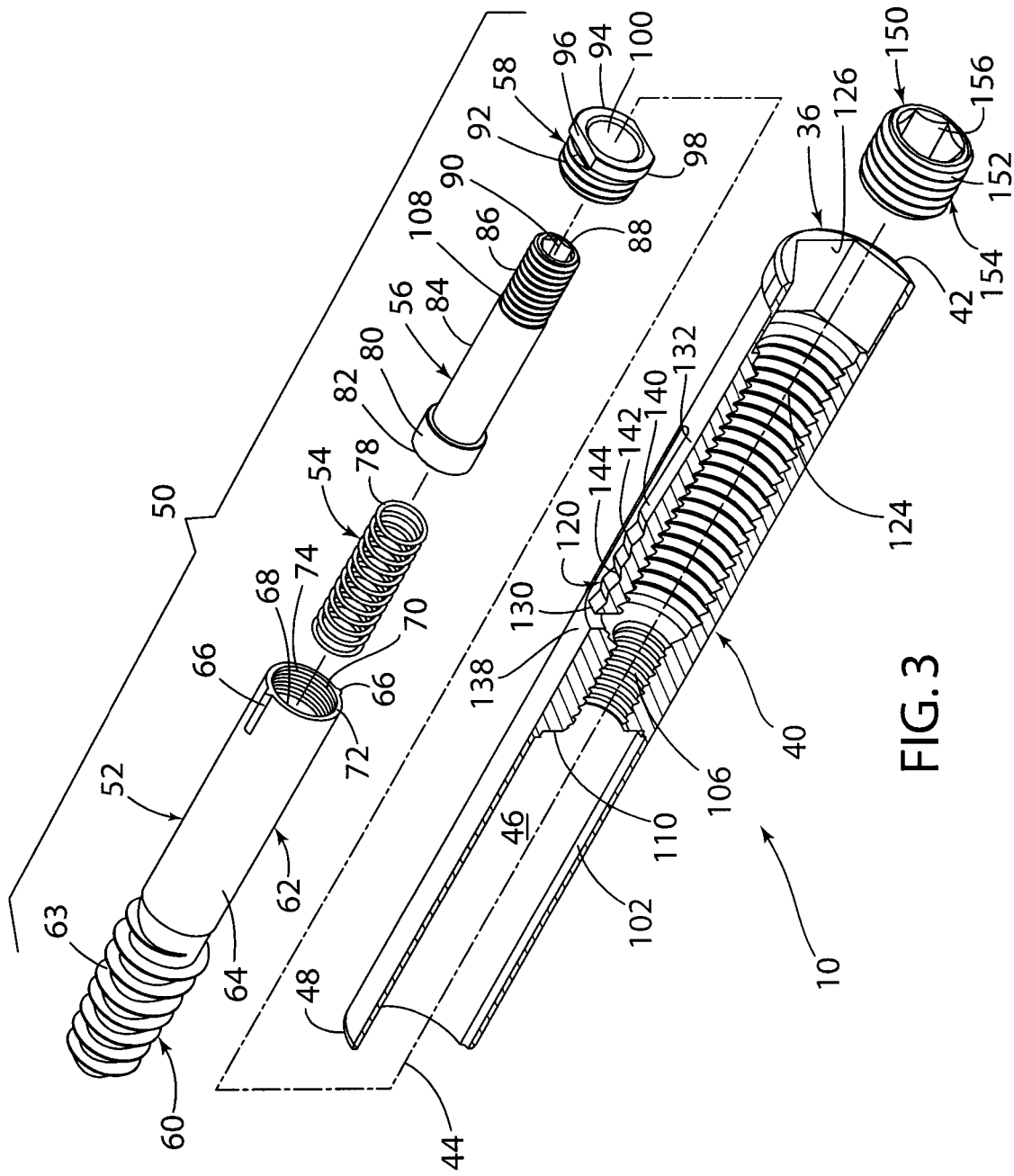
FIG. 3 is an exploded perspective view of a bone screw according to one embodiment of the present invention.
Figure 4:
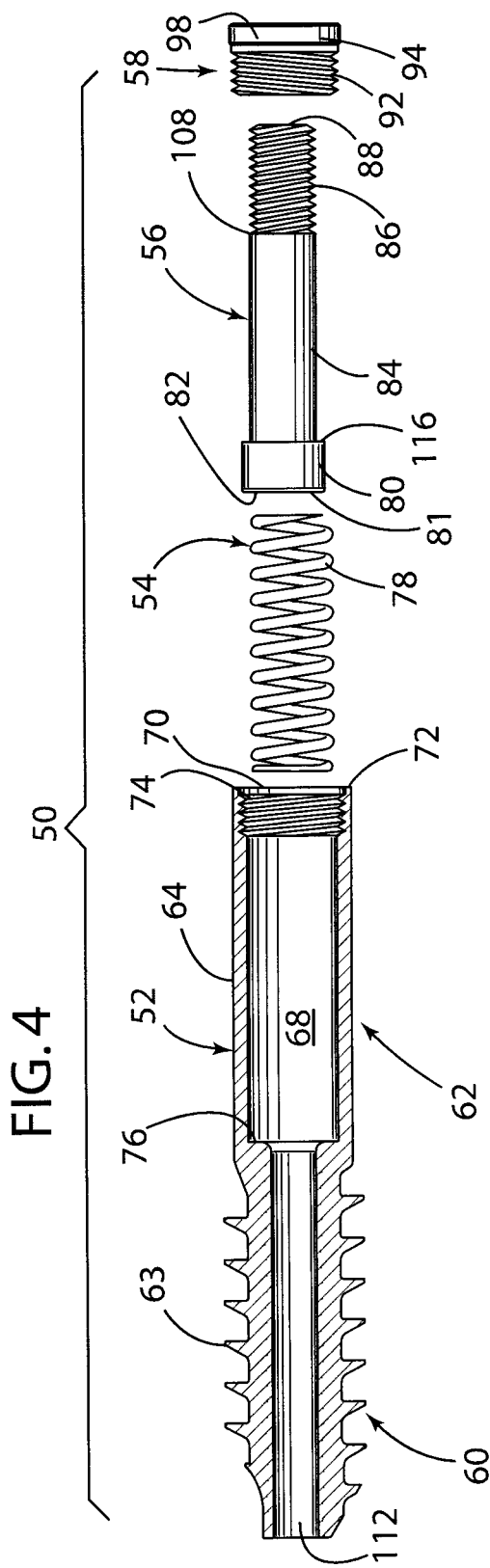
FIG. 4 is an exploded cross-sectional side view of a plunger assembly for use with a bone screw in accordance with one embodiment of the present invention.
Figure 5:
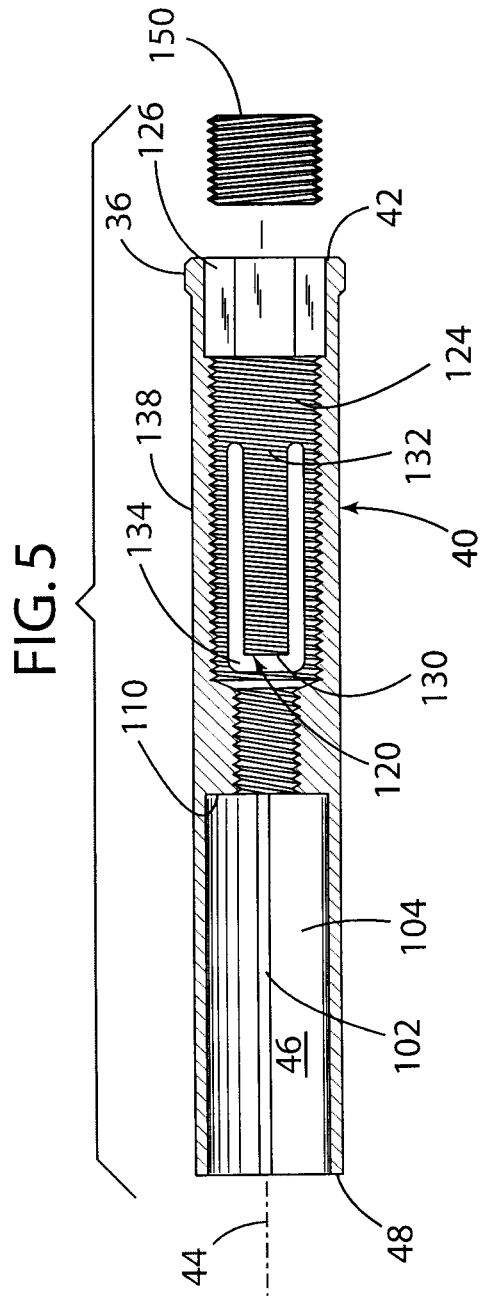
FIG. 5 is an exploded cross-sectional side view of a body for use with a bone screw in accordance with one embodiment of the present invention.

Referring now to FIG. 3, an exploded perspective view is shown of one embodiment of the bone screw 10 in accordance with the principles of the present invention. The bone screw 10 includes a cylindrical body or barrel 40 with the head 36 located at a first end 42 thereof. As illustrated, the head 36 is a lip or raised portion extending radially outward from the cylindrical body 40 of the bone screw 10. The head 36 operates as a stop or depth limiter whereby the head 36 of the bone screw 10 contacts or is seated on the outer cortex 38 of the femur 14.

The cylindrical body 40 includes several interior openings or apertures extending longitudinally along a longitudinal axis 44 of the bone screw 10. One of these interior openings is formed by a cylindrical shaped socket 46 that extends inwardly from a second end 48 of the cylindrical body 40. The socket 46 is sized to receive a plunger assembly 50 including a threaded plunger 52, a spring member 54, a guide member 56 and a retainer 58.

Turning for a moment to the plunger assembly 50, the threaded plunger 52 has a cylindrically shaped body including a threaded engagement portion 60 and a plunger portion 62. As illustrated, in FIGS. 4 and 9-11 the plunger portion 62 has a generally smooth cylindrical outer circumferential surface 64 located adjacent the threaded engagement portion 60. The threaded engagement portion 60 includes a plurality of helical threads 63. The helical threads 63 utilize a thread profile typical for use with bone screws. Detent tabs 66 extend radially outward from the cylindrical outer circumferential surface 64 of the plunger portion 62. While shown with two detent tabs 66 positioned generally opposite one another, a single or additional detent members can also be used.

The threaded plunger 52 further includes a generally cylindrical interior cavity or chamber 68 forming an opening 70 on one end 72 of the plunger portion 62. The chamber 68 includes a plurality of internal threads 74 extending into the chamber 68 from the end 72 of the plunger portion 62. The chamber 68 forms a generally cylindrical bore extending inward into the plunger portion 62 and terminating at a stop surface 76. In the present embodiment, the spring member 54 is shown as a coiled compression spring 78 sized to fit within the chamber 68.

As illustrated in FIGS. 3-4 and 12-15 the guide member 56 of the plunger assembly 50 has a generally cylindrical head 80 located on one end 82 thereof. That head 80 having a radially extending flat front face 81. The guide member 56 further includes a shank portion 84 connected to the head 80. The shank portion 84 being generally cylindrical and having a plurality of threads 86 is located adjacent an end 88 opposite the head 80. A hexagonal shaped drive socket 90 is located in the end 88 of the guide member 56. While shown as having a hexagonal shape, the drive socket 90 can be of various shapes including star or square provided they are suitable to accept a driving tool used to rotate the guide member 56.

As illustrated in FIGS. 3-4 and 16-19 the retainer 58 of the plunger assembly 50 includes a threaded portion 92 and a head 94. The threaded portion 92 having an outer diameter and thread configuration such that it is complementary to and threadably received in the threads 74 of the chamber 68 of the threaded plunger 52. The head 94 is generally cylindrical in shape and includes opposing flat surfaces 96 located on the outer peripheral surface 98 thereof. The retainer 58 further includes a cylindrical aperture or bore 100 that extends through the retainer 58.

As shown in FIG. 3 the plunger assembly 50 is generally assembled by inserting the coiled compression spring 78 into the chamber 68 of the threaded plunger 52 through the opening 70. The compression spring 78 extends between the stop surface 76 and the internal threads 74 located at the end 72 of the threaded plunger 52. The head 80 of the guide member 56 is inserted into the cavity or chamber 68 with the head 80 of the guide member 56 sized and shaped such that the head 80 slidably fits in the generally cylindrical cavity 68. For example, in the disclosed embodiment, the chamber 68 is generally cylindrically shaped and the head 80 of the guide member 56 is also generally cylindrically shaped. It should be understood however, that other complementary configurations could also be used. Once the head 80 of the guide member 56 is placed in the chamber 68 and contacts the spring 78, the retainer 58 is placed over the guide member 56 by sliding the shank portion 84 of the guide member 56 through the aperture 100 of the retainer 58. The retainer 58 slides along the shank portion 84 until the threaded portion 92 of the retainer 58 engages the complementary threads 74 located in the opening 70 at the end 72 of the threaded plunger 52. The retainer 58 is then tightened using a suitable tool engaging the opposed flat surfaces 96 of the retainer 58 until the head 94 of the retainer 58 contacts and is secured to the end 72 of the threaded plunger 52. As illustrated in FIG. 6 in the expanded or uncompressed position the compression spring 78 forces the guide member 56 outward until the head 80 of the guide member 56 contacts the retainer 58.

Once assembled the plunger assembly 50 is then slidably secured in a non-rotatable telescopic relationship in the socket 46 of the body 40. As illustrated in FIGS. 3-5 and 22-23 the socket 46 of the body 40 includes a pair of opposed grooves or channels 102 extending radially outward from the inner circumferential surface 104 of the socket 46. The grooves 102 are sized such that they slidably receive the detent tabs 66 located on the threaded plunger 52. The grooves 102 and detent tabs 66 cooperate to prevent relative rotational movement between the plunger assembly 50 and the body 40 while allowing the plunger assembly 50 to move in a reciprocal or back and forth manner in the direction of the longitudinal axis 44 of the body 40.

As illustrated in FIGS. 6-7 the guide member 56 is used to secure the plunger assembly 50 to the body 40. To secure the plunger assembly 50 to the body 40, the plunger assembly 50 is inserted into the socket 46 with the detent tabs 66 placed in the grooves or channels 102 located in the socket 46. As illustrated in FIGS. 3-7, 20-22 and 25 the body 40 includes a threaded aperture 106 extending longitudinally along the longitudinal axis 44 of the body 40. The threads of the threaded aperture 106 are complementary to the threads 86 on the guide member 56. Accordingly, once the threads 86 of the guide member 56 contact the threaded aperture 106 a suitable drive tool (not shown) having a configuration complementary to the drive socket 90 located in the end 88 of the guide member 56, shown herein as having a hexagonal shape, is inserted into the body 40 from the first end 42 until it engages the drive socket 90 of the guide member 56. Rotating the drive tool rotates the guide member 56 until the shoulder 108 of the guide member 56 located between the threads 86 and the shank portion 84 is seated on the surface 110 forming the base or bottom of the socket 46.

FIGS. 3-7 also illustrate a second method for installing the guide member 56 in the threaded aperture 106, wherein a passageway 112 extends longitudinally through the threaded plunger 52 and a drive socket is formed on the front flat face 81 located on the end 82 of the head 80. Accordingly, a drive tool may extend through the passageway 112 and engage the drive socket formed in the front flat face 81 of the end 82 of the head 80 to rotate the guide member 56 and correspondingly secure the guide member 56 in the body 40.

FIGS. 6-7 show the bone screw 10 in accordance with one aspect of the present invention, the bone screw 10 fully extended as illustrated in FIG. 6 and fully compressed as illustrated in FIG. 7. The distance of travel 114 of the threaded plunger 52 with respect to the body 40 is determined by the distance between the stop surface 116, that is the shoulder formed at the junction of the shank portion 84 and the head 80 of the guide member 56, and the stop surface 110 formed at the bottom of the socket 46 of the body 40. Accordingly, varying the length of the shank portion 84, that is the distance between the stop surface 110 and the shoulder 108 of the guide member 56, varies the amount of travel and correspondingly the amount of longitudinal compression of the bone screw 10.

Varying the strength or spring constant k of the spring 78 varies the compressive force necessary to move the threaded plunger 52 through the distance of travel 114. For example, depending upon the weight and size of an individual and degree of severity of the fracture, the compressive force of the spring 78 can be changed or modified to provide a suitable resistance force. It should be understood that the resistance force need not be linear, but may vary over the distance of travel 114. Accordingly, the present invention allows for compression of a fracture when a load is applied, for example, when a patient stands and weight is transferred from the femoral head 32 to the femur 14, if necessary, the plunger assembly 50 allows movement of the threaded plunger 52 within the socket 46 of the body 40 enabling compression between the femoral head 32 and the femur 14. The preferred embodiment contemplates a distance of travel 114 of 10 mm, however this is for illustrative purposes only and the actual degree or distance of travel 114 may be greater or less than 10 mm.

As illustrated in FIGS. 1-5, 20-22 and 26 the bone screw 10 includes a detent member, seen generally at 120 and illustrated as a finger, that is driven radially outward by a drive assembly shown as a screw member or set screw 150. The detent member 120 engages the bone nail 16 and maintains a positional relationship between the body 40 of the bone screw 10 and the bone nail 16. The detent member 120 fixes the position of the body 40 of the bone screw 10 with respect to the bone nail 16 and prevents both sliding and rotating of the body 40 of the bone screw 10 with respect to the bone nail 16. Accordingly, the detent member 120 keeps the body 40 of the bone screw 10 in place while the plunger assembly 50 allows movement of the plunger member 52 independent of the body 40 whereby any compression or sliding between the femoral head 32 and femur 14 is compensated for by movement of the plunger assembly 50.

As illustrated, the body 40 includes a threaded bore 124 extending inwardly from the first end 42 toward the threaded aperture 106. As shown in the drawings the threaded aperture 106, which receives the guide member 56, is located between the first end 42 and the second end 48 of the body 40. An internal drive socket 126 is located adjacent the first end 42 of the body 40. As illustrated, the drive socket 126 has a hexagonal configuration shaped to accept a hexagonal drive tool, see FIGS. 33-35 used to rotate and install the bone screw 10.

FIGS. 20-22 and 26 illustrate the detent member 120 in greater detail. The detent member 120 of the present embodiment is a cantilevered member 128 having a free end 130 and a fixed end 132. A slot 134 extends along the sides 136 and free end 130 of the cantilevered member 128. The free end 130 of the cantilevered member 128 is configured such that in the initial or first position it remains at or below the outer circumferential surface or periphery 138 of the body 40. As shown in the illustrated embodiment, the outer surface 140 of the detent number 120 may move radially outward to a position past or above the outer circumferential surface or periphery 138 of the body 40. The outer surface 140 of the cantilevered member 128 may include a plurality of ridges and grooves 142, 144. While the inner surface 141 of the cantilevered member 128 has a threaded configuration identical to the threads of the threaded bore 124.

Figure 8:
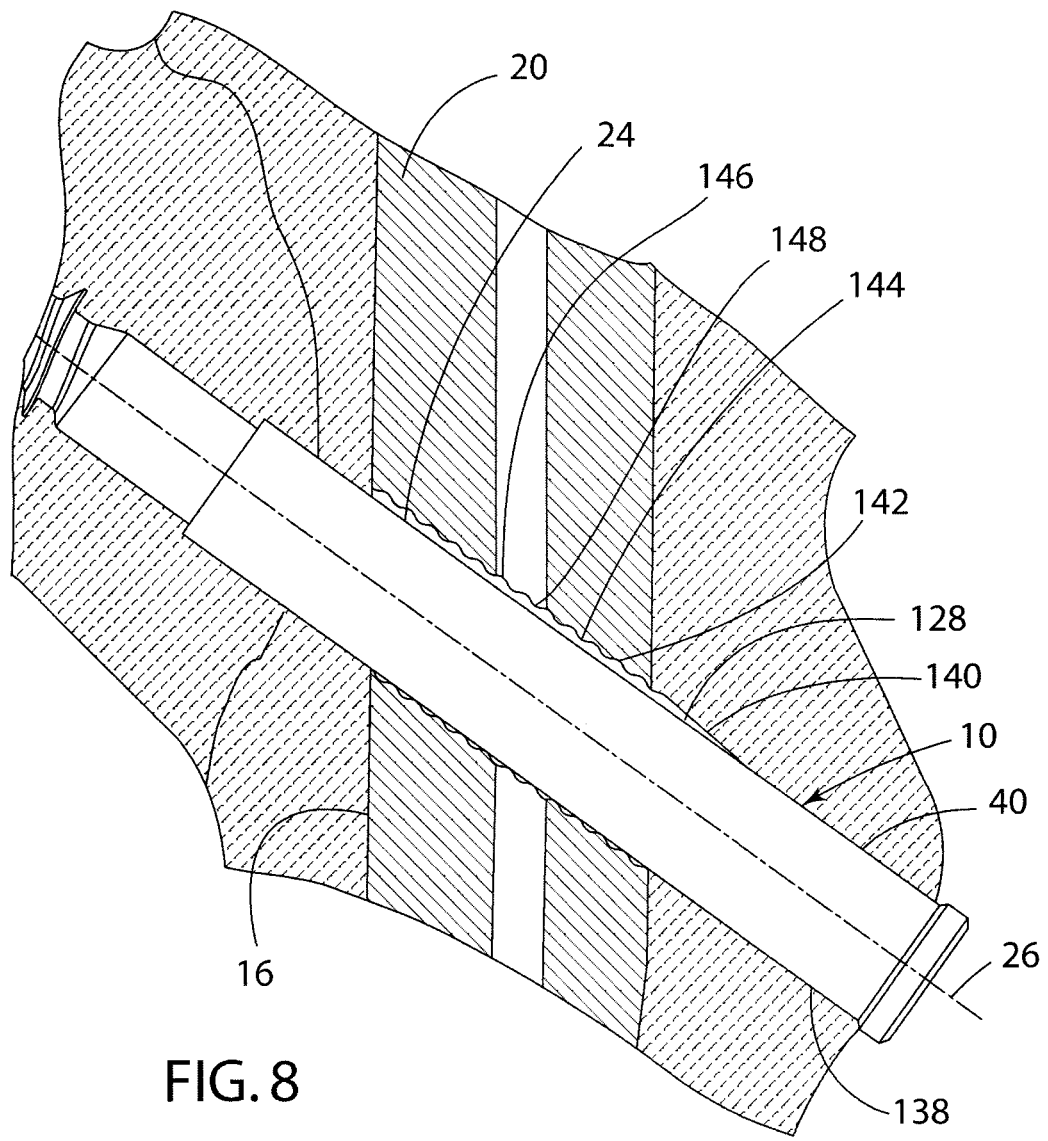
FIG. 8 is an enlarged schematic view of a bone screw according to a second embodiment of the present invention shown extending through the proximal end of a bone nail.
Figure 10:
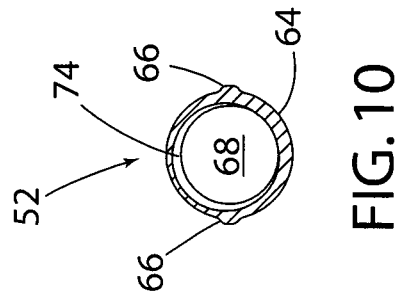
FIG. 10 is a cross-sectional view of the plunger of FIG. 9 taken along line 10-10.
Figure 9:
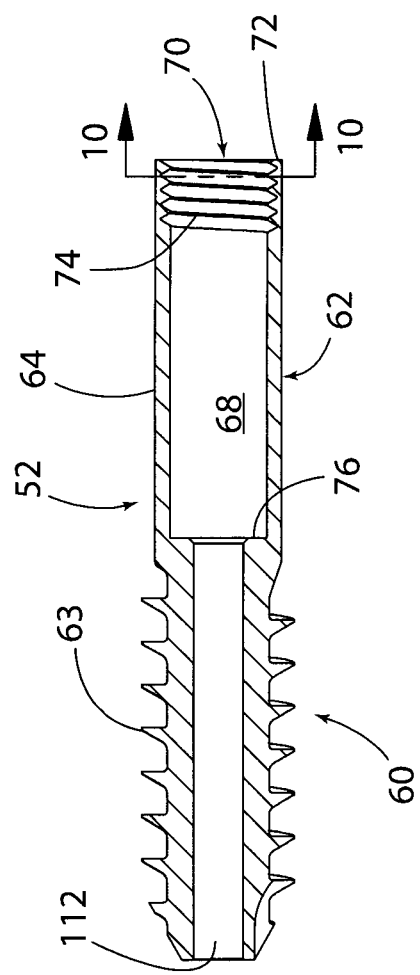
FIG. 9 is a cross-sectional view of the plunger of FIG. 11 taken along line 9-9.
Figure 11:
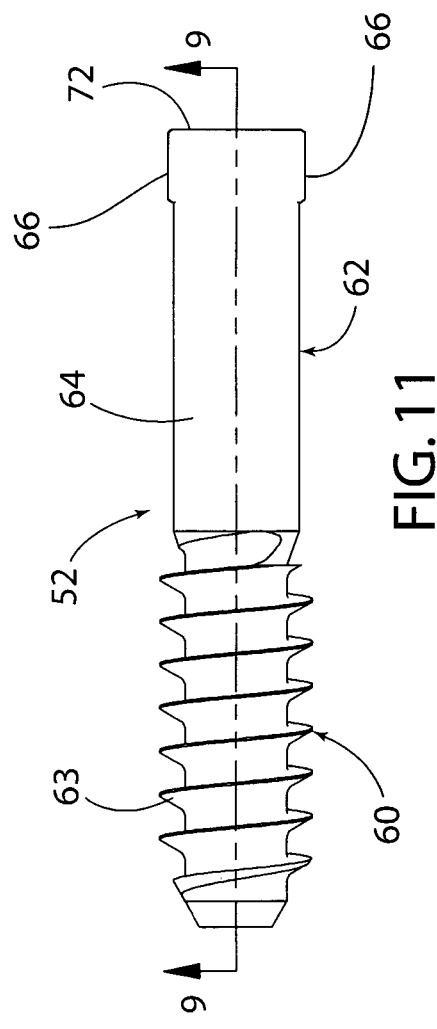
FIG. 11 is a side view of a plunger for use with a bone screw according to the present invention.
Figure 22:
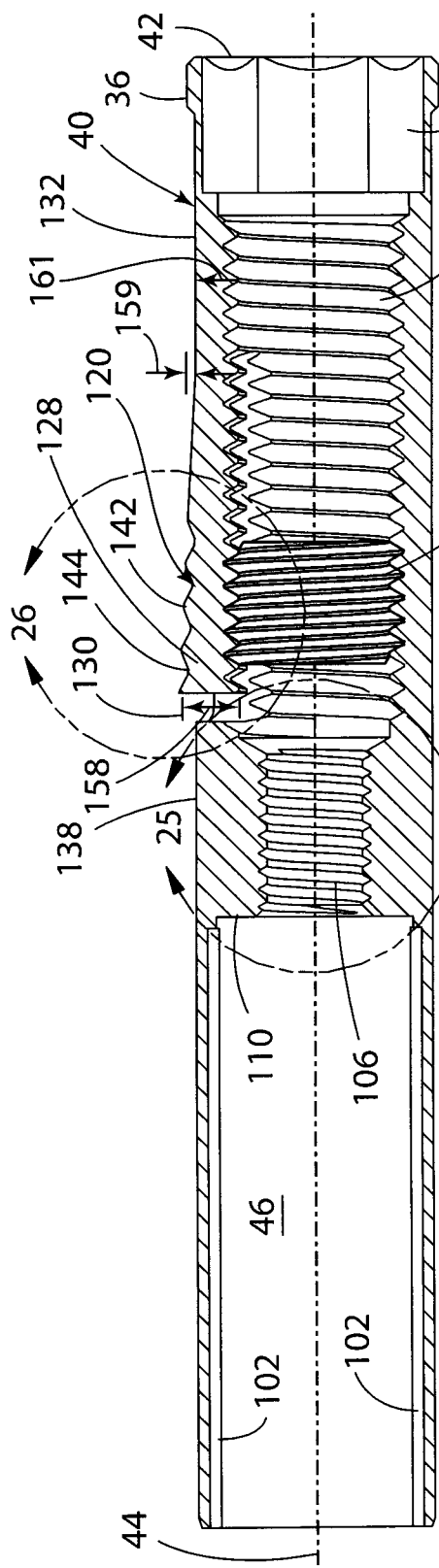
FIG. 22 is a cross-sectional side view, similar to that shown in FIG. 21, of a body for use with a bone screw illustrating the detent member extending outwardly past the outer surface of the body.
Figure 21:
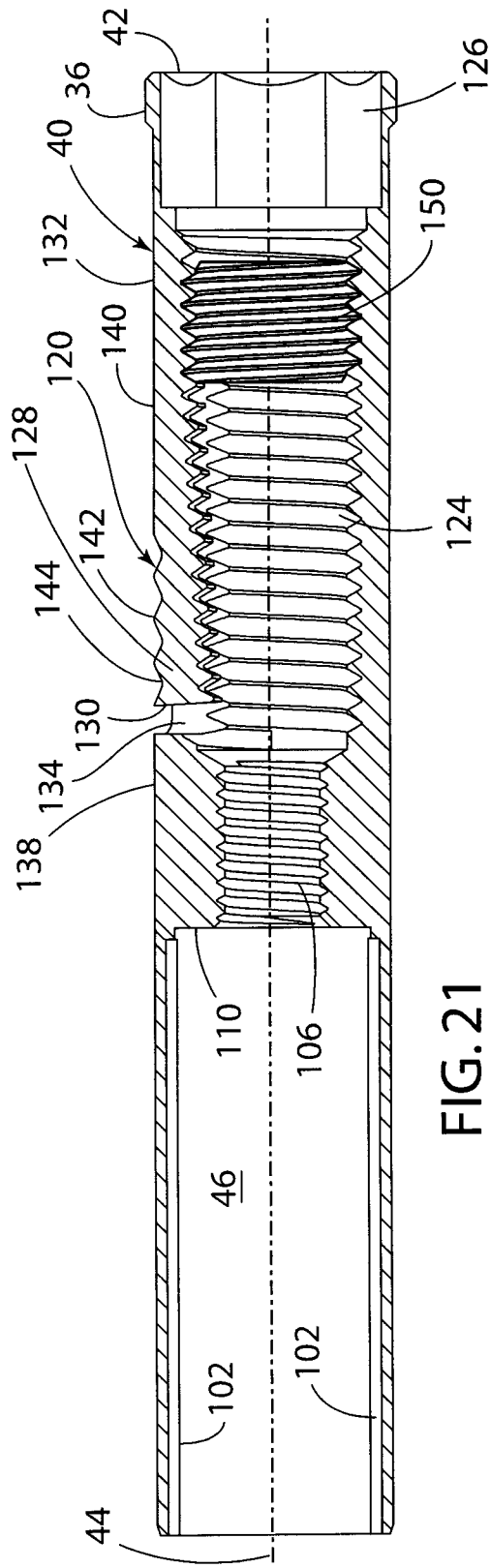
FIG. 21 is a cross-sectional side view of a body for use with a bone screw according to the present invention illustrating a detent member positioned flush with the outer surface of the body taken along lines 21-21 of FIG. 20.

As shown in FIG. 8 the plurality of ridges and grooves 142, 144 on the outer surface 140 of the cantilevered member 128 cooperate with corresponding and complementary ridges and grooves, 146 148 located in the aperture 24 extending through the proximal end 20 of the bone nail 16. While the cantilevered member 128 is disclosed with a plurality of ridges and grooves 142, 144 to aid in securing the bone screw 10 to the bone nail 16, this is but one embodiment. As illustrated in FIG. 2, the outer surface 140 of the cantilevered member 128 may be smooth with the corresponding interior surface of the aperture 24 in the proximal end 20 of the bone nail 16 also being smooth. Further, it is contemplated that the outer surface 140 of the cantilevered member 128 may include other configurations to increase the frictional or holding force between the detent member 120 and correspondingly the bone screw 10 and the bone nail 16. In addition, other surface configurations or coatings can be utilized to increase the holding force fixing the bone screw 10 in the aperture 24. While the outer circumferential surface or periphery 138 of the body 40 is disclosed herein without the ridges and grooves 142, 144 shown on the cantilevered member 128, the invention contemplates adding such ridges and grooves to the outer surface 138 of the body 40. Further, it is within the scope of the present invention to provide other types of surfaces or surface coatings that would reduce movement or rotation of the bone screw 10 with respect to the bone nail 16.

As illustrated in FIGS. 3, 20-22 and 26 one example of the drive assembly is shown in the present embodiment as a threaded member or set screw 150 having a plurality of threads 152 located on the outer peripheral surface 154 thereof wherein the set screw 150 threadably engages the threaded bore 124 of the body 40. The set screw 150 has a hexagonal bore 156 forming a drive socket suitable for receiving a driving tool, see FIGS. 33-35. The set screw 150 operates to urge the cantilevered member 128 radially outward as the set screw 150 travels inwardly along the threaded bore 124. The set screw 150 urges or drives the free end 130 of the cantilevered member 128 outwardly as it approaches the free end 130 since the wall or radial thickness 158 of the cantilevered member 128 is greater at the free end 130 of the cantilevered member 128 than the wall or radial thickness 161 at the fixed end 132 of the cantilevered member 128. Since the outer diameter of the set screw 150 remains constant, as it travels in the threaded bore 124 and along the length of the cantilevered member 128 it urges the free end 130 of the cantilevered member 128 outward whereby it extends above or past the outer peripheral surface 138 of the body 40 to a distance 159.

In one embodiment, the thickness of the free end 130 of the cantilevered member 128 is increased through the following steps, during manufacture of the body 40, the body 40 is turned to a predetermined outer diameter with a portion thereof, specifically the area where the cantilevered member 128 will be located, having a raised portion or section having a greater outer diameter. The magnitude or difference in the respective outer diameters being the amount or distance 159 that the free end 130 of the cantilevered member 128 will extend above or outwardly past the outer circumferential surface or periphery 138 of the body 40. In one embodiment, the raised section may have a conical shape beginning roughly at or corresponding to the location of the free end 130 of the cantilevered member 128 and tapering off to the overall diameter of the body 40 as it approaches the first end 42. Cutting the slot 134 forms the cantilevered member 128. Once formed, the cantilevered member 128 is depressed or forced inward into the threaded bore 124 while the remaining raised portion or section is removed whereby the entire outer circumferential surface or periphery 138 of the body 40 has a constant outer diameter. In the embodiment wherein the outer surface 140 of the cantilevered member 128 includes ridges and grooves 142, 144 these can be formed prior to cutting the slot 134 and moving the free end 130 of the cantilevered member 128 inward prior to removing the remaining raised portion or section. It is within the scope of the present invention to use other means to increase the thickness of the free end 130 of the cantilevered member 128 whereby as the set screw 150 travels through the threaded bore 124 it urges the free end 130 outwardly such that it engages the aperture 24 located in the proximal end 20 of the bone nail 16. For example, additional material could be added to the outer surface 140 of the cantilevered member 128 to increase its overall thickness.

Accordingly, the present invention contemplates a detent member 120 movable between a first position wherein the free end 130 of the cantilevered member 128 is positioned flush with or at the same level as the outer peripheral surface 138 of the body 40 and a second position wherein the free end 130 of the cantilevered member 128 extends above or past the outer peripheral surface 138 the body 40. While shown herein using a cantilevered member 128 formed as an integral part of the body 40, the present invention contemplates that the detent member 120 may also be inserted into the threaded bore 124 as a separate member wherein the separate member is still urged outwardly by the drive assembly and still come within the scope of the present invention.

Referring to FIGS. 31 and 32 there is shown an alternative embodiment of a body 340 for use with a bone screw 10 of the present invention. The body 340 includes first and second opposed detent members, seen generally at 342, urged outwardly by a set screw 344. The opposed detent members 342 are similar in design to those disclosed in the previous embodiment in that the detent members 342 include cantilevered members 346 having a fixed end and a free end 348, 350. The free end 350 once again having a wall or radial thickness 352 greater than the wall or radial thickness at the fixed end 348. The alternative embodiment also discloses the outer surface 354 of the cantilevered members 346 as smooth rather than with the ridges and grooves of the previous embodiment.

Figure 33:
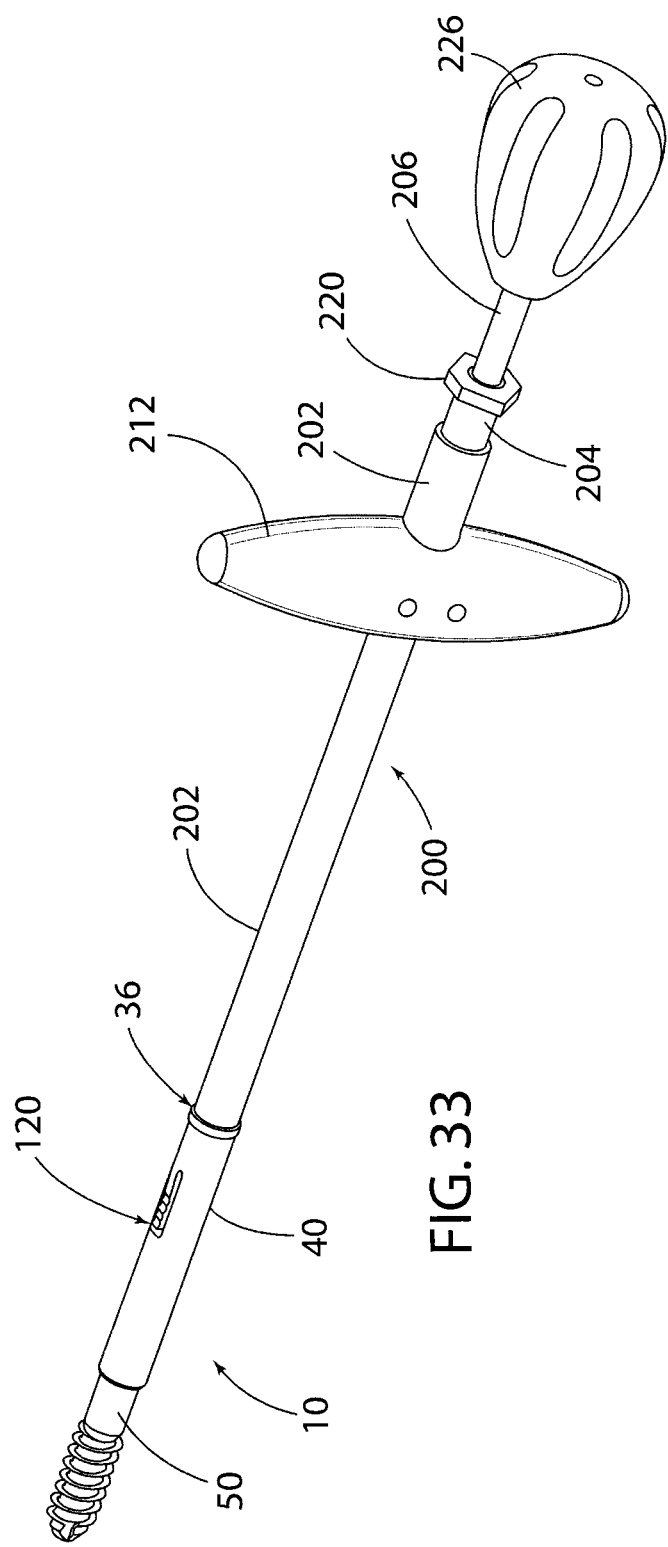
FIG. 33 is a perspective view of installation equipment used for installing a bone screw according to the present invention.
Figure 34:
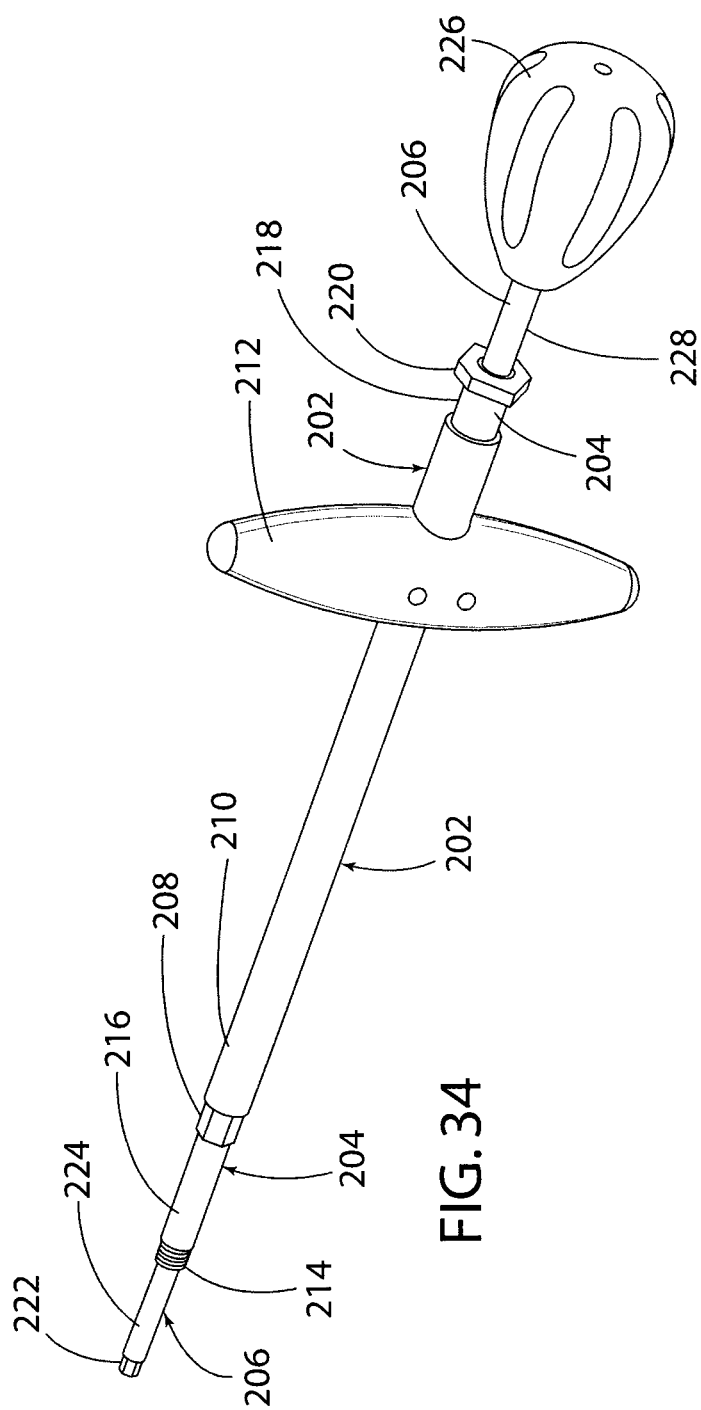
FIG. 34 is a perspective view of the installation equipment and the bone screw.
Figure 35:
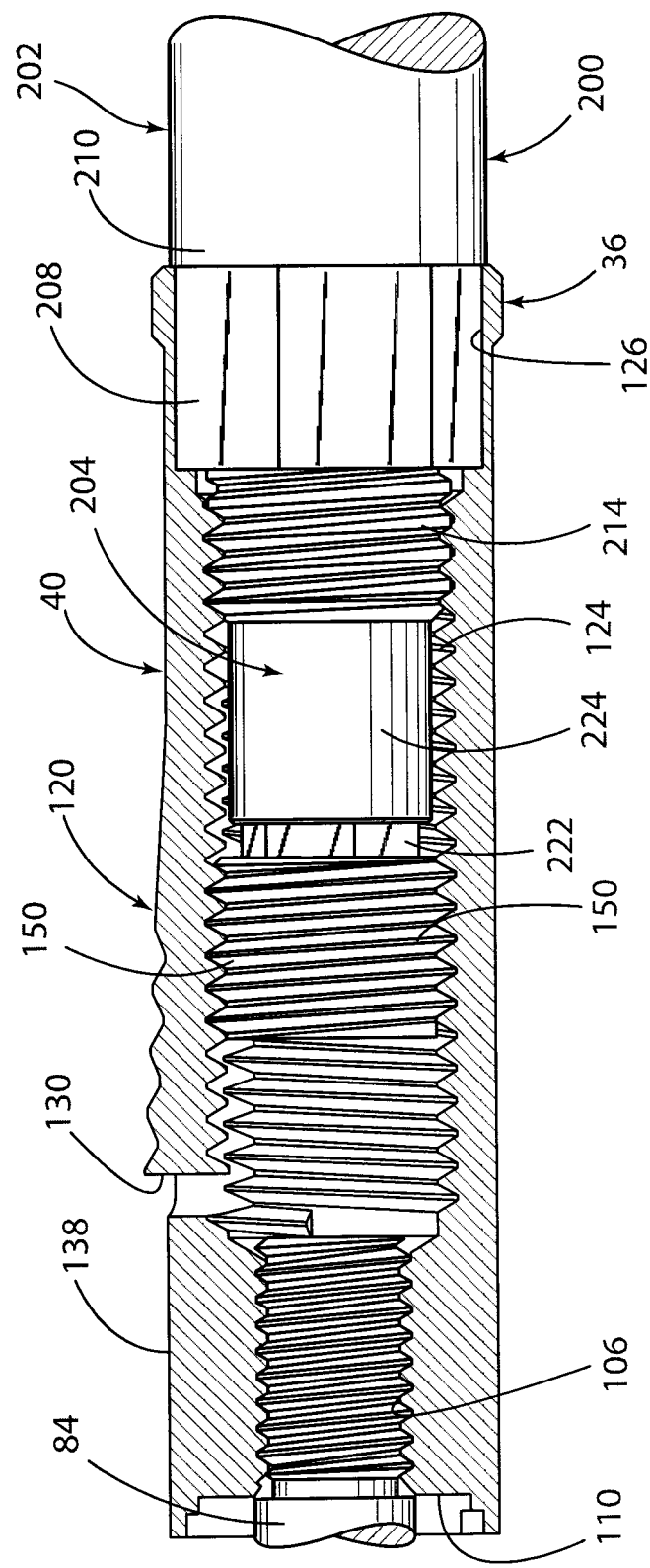
FIG. 35 is a cross-sectional view illustrating the installation equipment connected to the bone screw according to the present invention.

Turning now to FIGS. 33-35 an installation tool, seen generally at 200, for use in installing the bone screw 10 according to the present invention is shown. The installation tool 200 includes a first or outer drive member or driver 202, a second or middle drive member or driver 204 disposed within the first or outer drive member 202 and a third or inner drive member or driver 206 disposed within the second or middle drive member 204. The outer drive member 202 is a hollow rod or shaft having a hexagonal shaped drive portion 208 located on the end 210 thereof. A handle 212 is located at the opposite end and is attached to the outer driver 202 whereby rotation of the handle 212 rotates the outer driver 202. The middle driver 204 includes a threaded portion 214 located on an end 216 and the opposite end 218 of the middle driver 204 includes a head 220 configured to accept a tool used to rotate the middle driver 204 independent of the outer driver 202. The middle driver 204 is also a hollow member and the inner driver 206 is nested within the middle driver 204. A hexagonal shaped drive member 222 is attached to one end 224 with a handle 226 attached to the opposite end 228.

FIG. 35 illustrates the engagement between the installation tool 200 and the bone screw 10. Specifically, the threaded portion 214 of the middle driver 204 threadably engages the threaded bore 124 and a suitable drive tool (not shown) contacts the head 220 of the middle driver whereby the operator can tighten and securely attach the bone screw 10 to the installation tool 200. The outer driver 202 then slides over the middle driver 204 until the hexagonal shaped drive portion 208 engages the hexagonal shaped drive socket 126 of the bone screw 10. It should be understood that rotation of the handle 212 rotates the entire bone screw 10 such that the operator can properly insert the bone screw 10. Once the bone screw 10 is placed in its proper position within the femoral head 32, the inner driver 206 is then slid forward within the middle driver 204 until the hexagonal shaped drive portion 222 thereof engages the hexagonal shaped bore 156 of the set screw 150. Accordingly, rotation of the handle 226 attached to the inner driver 206 correspondingly rotates and moves the set screw 150 inwardly towards the free end 130 of the cantilevered member 128 whereby the operator forces or drives the detent member 120 outwardly into engagement with the aperture 24 located in the proximal end 20 of the bone nail 16. It should be understood that the handle 226 located on the inner driver 206 may have some type of torque limiting or clutch arrangement that limits the amount of torque applied to the set screw 150 which correspondingly limits the force generated by the detent member 120. While not necessary, it is contemplated that the use of such a torque limiting device or handle can be used to control the pressure applied by the detent member 120 and prevent over tightening and possible damage to the bone screw 10.

Figure 36:
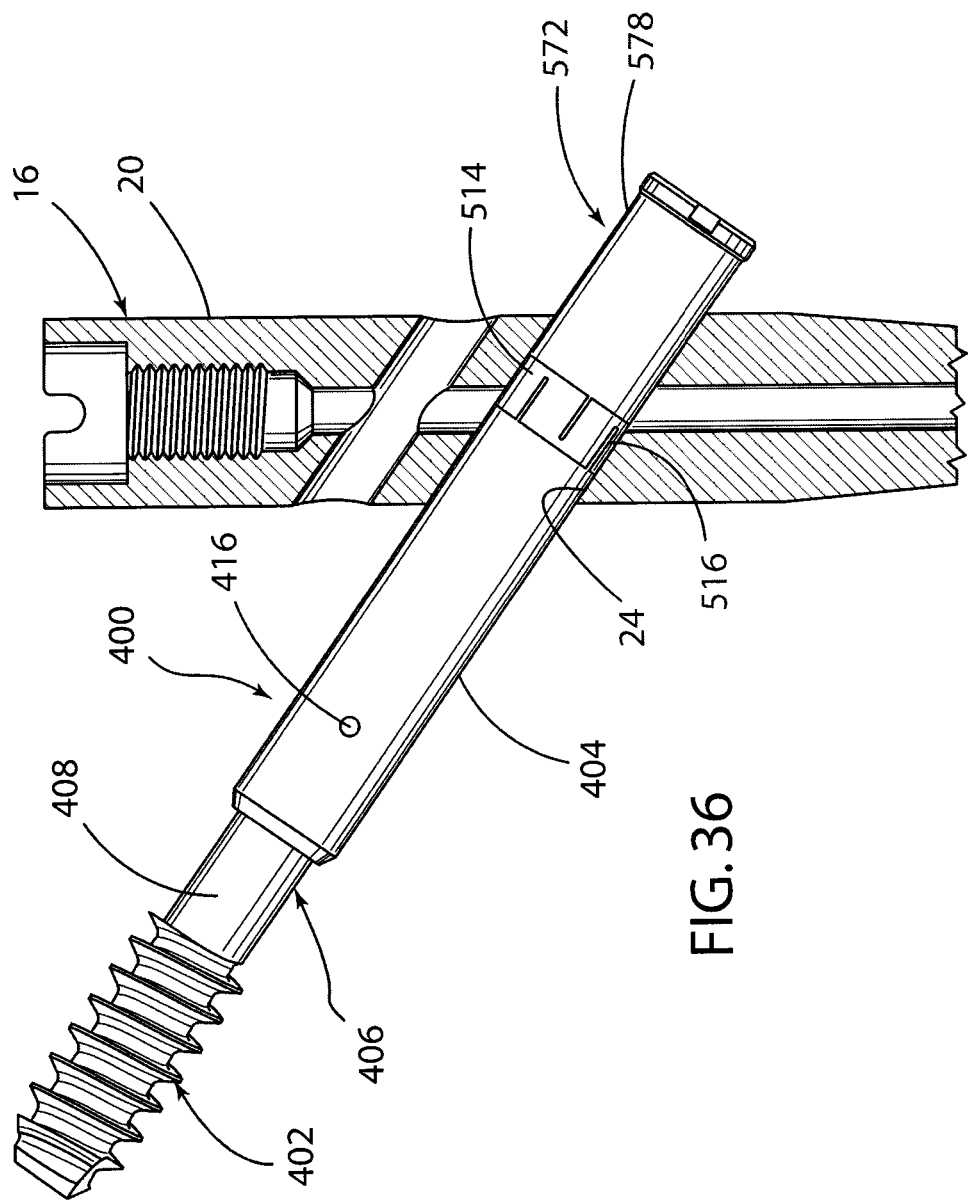
FIG. 36 is an enlarged schematic view of a bone screw according to one embodiment of the present invention shown extending through the proximal end of a bone nail.

FIG. 36 illustrates a schematic view of an alternative embodiment of a bone screw, seen generally at 400, according to the present invention. Similar to the previous embodiment, the bone screw 400 is part of the fixation system 12 illustrated in FIG. 1. As with the previous embodiment, the bone screw 400 extends through an aperture or throughbore 24 extending through the proximal end 20 of the bone nail 16 such that a threaded portion 402 of the bone screw 400 extends through the femoral neck 30 of the femur 14 and into the dense cortical bone of the femoral head 32. The bone screw 400 spans the fracture illustrated in FIG. 1 as the jagged line 34.

As set forth more fully herein, the bone screw 400 includes a cylindrical body or barrel 404 and a plunger assembly 406 including a plunger 408. Similar to the previous embodiment, the bone screw 400 may include a detent assembly, seen generally at 512, including a lock ring 514 that engages the body 404 of the bone screw 400 to maintain a positional relationship between the body 404 of the bone screw 400 and bone nail 16. As set forth below, the lock ring 514 helps keep the body 404 of the bone screw 400 in place while the plunger assembly 406 allows movement of the plunger 408 independent of the body 404. The bone screw 400 may include either the plunger assembly 406 or the detent assembly 512, or it may include both.

Figure 37:
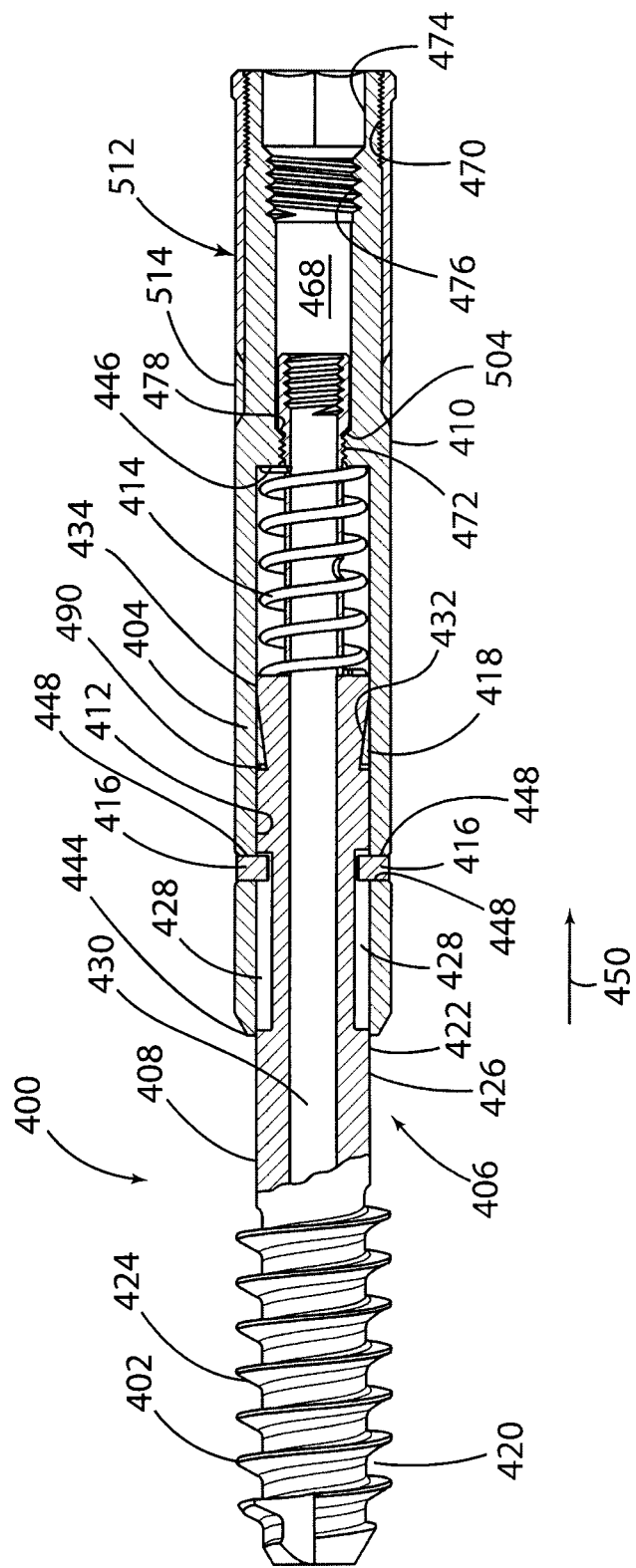
FIG. 37 is a cross-sectional side view of a bone screw according to one embodiment of the present invention with the plunger assembly extended.
Figure 39:
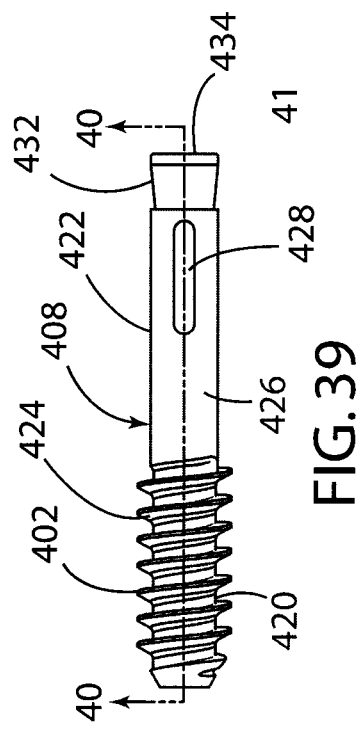
FIG. 39 is a side view of the plunger of FIG. 38.
Figure 40:
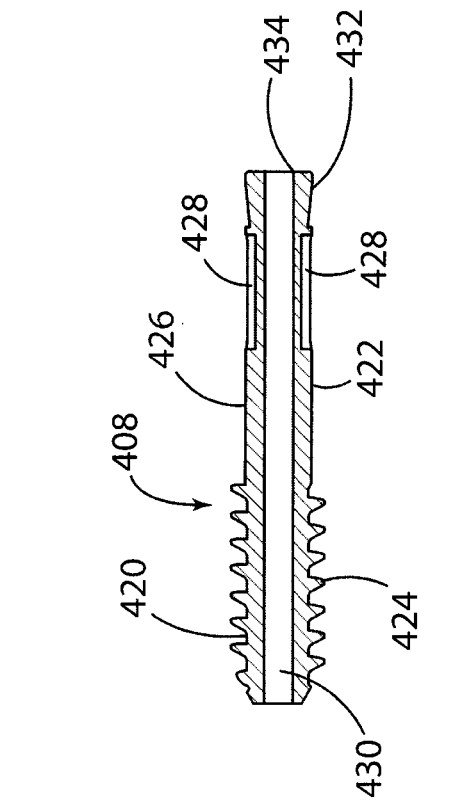
FIG. 40 is a cross-sectional side view of the plunger of FIG. 38 taken along line 40-40.
Figure 38:
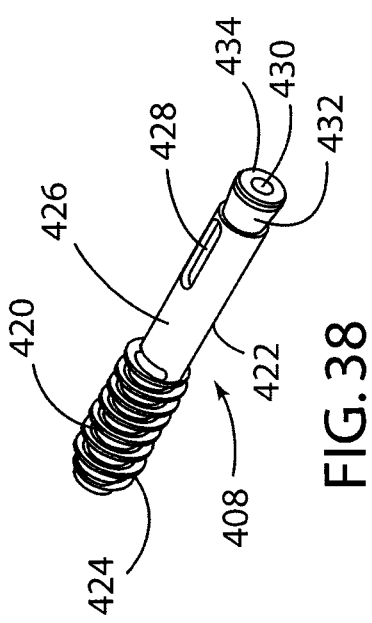
FIG. 38 is a perspective view of a plunger for use with a bone screw according to one embodiment of the present invention.
Figure 41:
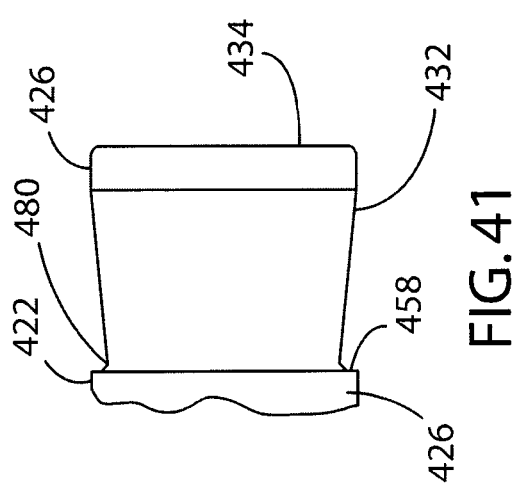
FIG. 41 is an enlarged side view of one end of the plunger of FIG. 38.

FIG. 37 shows a cross-sectional side view of the bone screw 400 in accordance with the principles of the present invention. The bone screw 400 includes a cylindrical body or barrel 404 having an outer circumferential surface 410 and a socket 412 sized to receive the plunger assembly 406 which includes the plunger 408, a spring member 414, a pair of retaining pins 416 and a latch or detent mechanism, illustrated in the present embodiment as an annular wedge 418. The plunger 408 is telescopically disposed within the socket 412 located in the cylindrical body or barrel 404. The latch or detent mechanism operates to allow relative movement between the plunger 408 and cylindrical body or barrel 404 in one direction while limiting movement between the plunger 408 and cylindrical body or barrel 404 in the opposite direction. Accordingly, as the bone screw 400 is compressed the plunger 408 will move in but not out.

As illustrated in FIGS. 37-41, the plunger 408 includes a threaded portion 420 and a piston portion 422. The threaded portion having a plurality of helical threads 424 configured in a tooth profile typical for use with bone screws. The piston portion 422 having a generally smooth cylindrical outer circumferential surface 426 sized to slidably fit within the socket 412 of the cylindrical body 404. The piston portion 422 further including a pair of longitudinally extending grooves or channels 428 located on the outer circumferential surface 426 of the piston portion 422. While two longitudinally extending grooves 428 are shown, single or multiple grooves can also be used. The plunger 408 also has a longitudinally extending aperture or passageway 430 enabling the plunger assembly to pass over a guide wire used for inserting the bone screw 400.

The plunger 408 further includes an inwardly beveled or tapered conical portion 432 located on the piston portion 422 adjacent the end 434 thereof opposite the threaded portion 402. As illustrated, the conical portion 432 extends radially inwardly as it extends from a position near the end 434. The conical portion 432 terminates on one end at a front surface or shoulder 458. The conical portion 432 cooperates with the annular wedge 418, functioning as a latch or detent mechanism, to control travel of the plunger 408 within the cylindrical body 404, specifically the socket 412 of the bone screw 400. As illustrated in FIGS. 42-45 the annular wedge 418 includes a forward or leading end 456 and a rear end, an outer surface 436 having a plurality of pitched teeth 438 and a beveled or tapered conical inner surface 440 extending inwardly such that the radial thickness is greater at the forward or leading end 456. The annular wedge 418 further includes a slot 442 extending the length thereof whereby the annular wedge 418 may function as a split ring that can be expanded or compressed. The conical portion 432 of the outer surface 426 of the plunger 408 is complementary to the conical inner surface 440 of the annular 418. With the forward or leading end 456 of the annular member 418 placed adjacent the front surface or shoulder 458 of the conical portion 432, the annular member 418 may move longitudinally along the conical portion 432 of the plunger 408.

Figure 51:
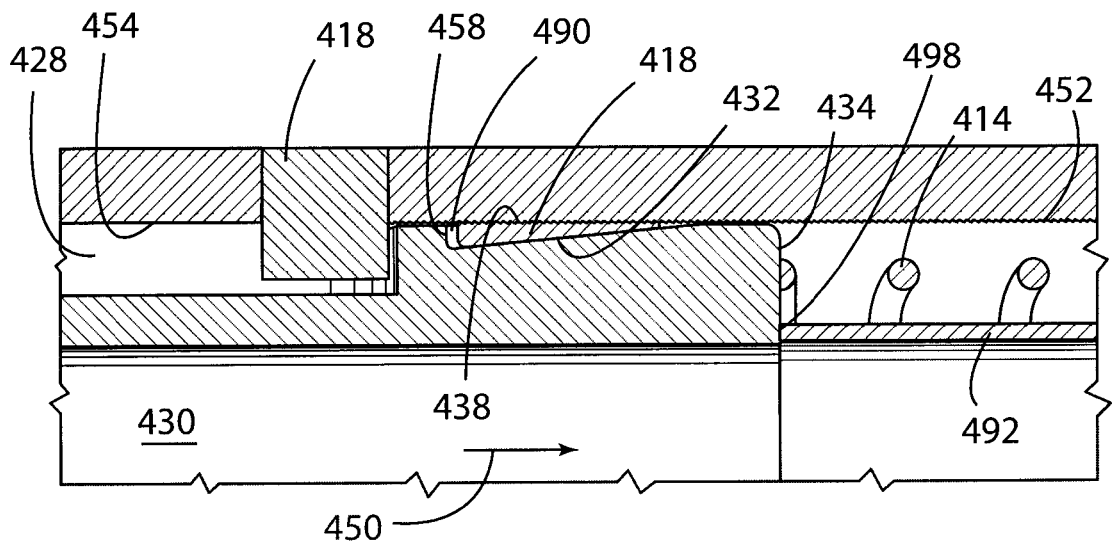
FIG. 51 is an enlarged cross-sectional schematic side view of a bone screw according to the present invention.
Figure 52:
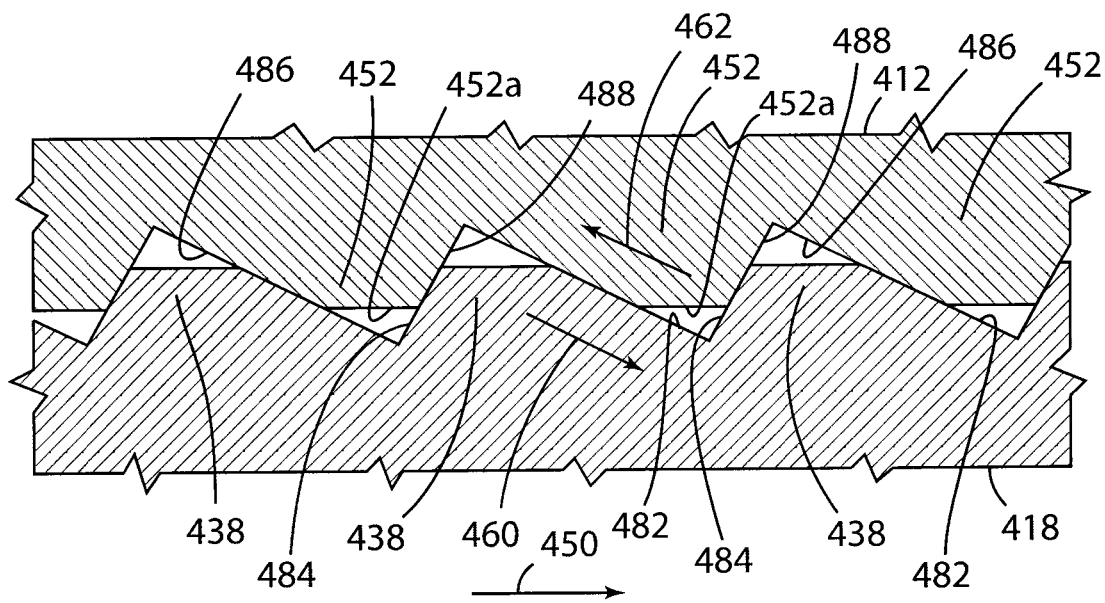
FIG. 52 is an enlarged cross-sectional schematic side view illustrating the engagement between respective teeth of the annular wedge and body.

As illustrated in FIGS. 51-52 the pitched teeth 438 of the annular wedge 418 have a ramp surface 482 and an engagement surface 484. In addition, the pitched teeth 452 located on the inner surface 454 of the socket 412 also have a ramp surface 486 and an engagement surface 488. The respective ramp and engagement surfaces 482, 484, 486, 488 are complementary and operate such that as the plunger 408 slides rearwardly into the socket 412 of the body 404, the respective ramp surfaces 482, 486 have a degree or angle enabling them to slide on one another and allow rearward movement. However, the respective engagement surfaces 484, 488 have a degree or angle preventing movement in the outward direction or in a direction opposite the arrow 450.

In addition, while the degree of the tapered portions of the respective plunger 408 and annular wedge 418 is the same, the longitudinal length of the conical portion 432 on the plunger 408 is slightly longer than the width of the annular wedge 418. Whereby the annular wedge 418 may slide on or move longitudinally along the conical portion 432 of the outer surface 426 of the plunger 408 as the annular wedge 418 is driven radially inward by respective ramp surfaces 482, 486 and into the gap or open area 490 created by the conical portion 432 as set forth below.

As illustrated in FIGS. 46-50, the socket 412 of the cylindrical body or barrel 404 extends inwardly from an end 464 thereof adjacent the opening 444 of the socket 412. The body 404 further includes a second socket or passageway 468 extending inwardly from the opposite end 470 of the body 404. A threaded passageway 472 extends between the respective first and second sockets 412, 468. Similar to the previous embodiment, the body 404 further includes an internal drive socket 474 shown herein having a hexagonal configuration to accept a hexagonal drive tool used to rotate and install the bone screw 400. Adjacent the hexagonal drive socket 474 is a plurality of internal threads forming a threaded bore 476 that correspondingly receives the threaded portion of an installation tool, similar to that illustrated in FIG. 34.

The plunger assembly of 406 also includes a lockout tube 492 illustrated in FIGS. 53-54. The lockout tube 492 is a tubular body 494 having a longitudinal aperture or passageway 496. The lockout tube 492 includes a first end 498 and a second end 500 with a head portion 502 located adjacent the second end 500. A shoulder 504 forms the transition between the head portion 502 and the tubular body 494. A plurality of right-handed threads 506 are located on the outer surface 508 of the tube body 494 adjacent the shoulder 504.

The head portion 502 includes a plurality of left-handed threads 510 located on an inner surface of the passageway 496. As set forth below, when installed in the body 404 the first end 498 of the lock out tube 492 will engage the end 434 of the plunger 408 when the plunger 408 is inserted into the socket 412 and prevent movement of the plunger 408 until the lockout tube 492 is removed.

Typically, fitting together the plunger assembly 406 first requires inserting the lockout tube 492 into the body 404 by inserting the lockout tube through the second socket or passageway 468 wherein the tubular body 494 passes through the threaded passageway 472. The tubular body 494 continues through the threaded passageway until the threads 506 of the lockout tube 492 engage the threaded passageway 472 and the lockout tube 492 is rotated to engage the threads and ultimately tightened until the shoulder 504 of the lockout tube 492 contacts the engagement surface 478 to secure the lockout tube 492

Once the lockout tube 492 is inserted and secured, assembly continues by inserting the spring member 414 into the socket 412 through the opening 444. The spring member 414 extends between a bottom or end surface 446 of the socket 412 and the end 434 of the plunger 408. The spring member 414 is a compression spring that operates to urge the plunger 408 outwardly in a direction opposite the arrow 450, see FIG. 37. After inserting the spring member 414, the plunger 408 is inserted inwardly into the socket 412 until the end 434 of the plunger 408 contacts the first end 498 of the lockout tube 492 preventing further inward travel. After the plunger 408 is placed and located in the socket 412 A pair of retaining pins 116 are placed in and extend through the respective apertures 448 in the cylindrical body 404. The grooves or channels 428 in the plunger 408 receive the retaining pins 116 and initially act in conjunction with the lockout tube 492 to prevent movement of the plunger 408 with respect to the body 404 prior to installation of the bone screw 400.

In addition, the grooves or channels 428 perform several other functions. They limit the longitudinal travel of the plunger 408 in the socket 412, with the amount of travel limited by the length of the groove or channel 428. They also prevent rotation of the plunger 408 with respect to the cylindrical body 404 such that rotation of the cylindrical body 404 also rotates the plunger 408. Further, the retaining pins 416 take up any shear load existing between the plunger 408 and the cylindrical body 404 occurring during insertion of the bone screw 400 into the bone, that is, rotation of the bone screw 400.

Providing the cylindrical socket 412 and plunger 408 with complementarity shapes enables a telescopic relationship between the two while preventing respective relative rotation. Different cross-sections or configurations can be used, for example a square cross-section, to prevent rotation from occurring between the cylindrical body 404 and plunger 408 while allowing sliding or telescopic movement between the body 404 and plunger 408. Such cross-sections or configurations will allow the plunger 408 to slide or move in a reciprocal manner in the direction of the longitudinal axis of the body 404 within the socket 412 while maintaining a positional relationship between the two components so that they rotate together.

As set forth below, after removal of the lockout tube 492, the annular wedge 418 operates in conjunction with the spring member 414 to control the movement of the plunger 408 within the socket 412. In the present embodiment, the annular wedge 418 operates to limit movement of the plunger 408 only in the direction of the arrow 450. That is, the plunger 408 can collapse or extend inwardly into the socket 412 when compressed against the spring member 414; however, once collapsed the annular wedge 418 prevents the plunger 408 from returning to its pre-collapsed position.

FIGS. 45, 49 and 51-52 illustrate the cooperation of the pitched teeth 438 located on the outer surface 436 of the annular wedge 418 with the pitched teeth 452 located on the inner surface 454 of the socket 412. As illustrated, movement of the plunger 408 with respect to the body 404 is controlled by cooperation between the teeth 438 of the annular wedge 418 and the teeth 452 located on the inner surface 454 of the socket 412. Specifically, the complementary pitched teeth 438, 452 on the respective surfaces provides for a collapsible bone screw 400 having a plunger 408 capable of being held in a collapsed or compressed position. The annular wedge 418 includes a slot 442. The slot 442 enables radial expansion and contraction of the annular wedge 418. Installing the annular wedge on the plunger 408 includes expanding the annular wedge 418 and sliding it over the rear end 434 of the plunger 408. The annular wedge 418 slides over the rear end 434 of the plunger 408 until it engages and snaps into the conical portion 432 of the plunger 408. The annular wedge 418 fits loosely about the conical portion 432 of the plunger 408. Specifically, when expanded, the overall diameter of the annular wedge 418 is greater than the overall diameter of the plunger 408. That is, the outer surface 436 or top of the pitched teeth 438 of the expanded annular wedge 418 extend above the outer circumferential surface 426 of the plunger 408.

In addition, the cavity or depression 480 formed in the plunger 408 by the inwardly tapered conical portion 432 is sized slightly larger than the shape of the annular wedge 418. Accordingly, when compressed, the overall outer diameter of the annular wedge 418 is slightly less than the overall diameter of the plunger 408. The flat surface 452a of the tooth 452 has the same inner diameter as the inner surface 454 of the socket 412. Accordingly, compression of the annular wedge 418 into the cavity or depression 480 formed by the tapered conical portion 432 provides necessary clearance between the inner surface 454 of the socket 412 of the body 404 and the outer surface 436 of the annular wedge 418. Further, as illustrated in FIG. 52 the ramp surfaces 482 pitched teeth 438 of the annular wedge 418 slide over the respective ramp surfaces 486 of the pitched teeth 452 located on the inner surface 440 of the body 404.

Accordingly, a load applied to the fracture that tends to compress or reduce the fracture acts against the compressive force of the spring and moves or drives the plunger inwardly and compresses the spring 414. As the plunger 408 extends rearwardly, into the socket, in the direction of the arrow 450, the respective pitched teeth 438 of the annular wedge 418 slide over the pitched teeth 452 of the inner surface 454 of the cylindrical body 404 allowing for collapse or inward travel of the plunger 408 within the socket 412, see FIG. 52. Arrows 460, 462 illustrate the movement as the respective teeth 438, 452 slide over one another when the plunger 408 moves in the direction of the arrow 450. As set forth above, the respective teeth 438, 452 each include a ramp surface 482, 486 and an engagement surface 484, 488. When the plunger 408 is compressed inwardly the respective ramp surfaces 482, 486 operate together to compress the annular wedge 418 inwardly into the conical portion 432 of the plunger 408. Specifically, the ramp surfaces 482, 486 cause a cam action between the teeth 438, 452 that drives the annular wedge 418 inwardly and to the left, that is, into the gap or open area 490. Placing the forward or leading edge 456 of the annular wedge 418, the edge adjacent the thicker portion of the annular wedge 418, adjacent the shoulder or front surface 458 of the conical portion 432. Whereby the conical portion 432 provides a recess that receives the annular wedge 418 during inward travel of the plunger 408.

As illustrated in FIG. 51, the annular wedge 418 operates to prevent outward travel of the plunger; that is, in a direction opposite the arrow 450. Since the annular wedge 418 is outwardly biased, or preloaded in an outwardly expanded mode, whereby the respective teeth 438, 452 of the annular wedge 418 and the cylindrical body 404 are engaged, the annular wedge 418 resists any outward or forward travel by the plunger 408. Specifically, the engagement surfaces 484, 488 of the respective teeth, 438, 452 are typically pitched at an angle that does not to allow movement of the annular wedge 418 in a direction opposite that of the arrow 450. In addition, the bevel or taper of the conical portion 432 cooperates with the beveled or tapered inner surface 440 of the annular wedge 418. Since the respective teeth 438, 452 of the annular wedge 418 and body 404 remains in contact any forward motion of the annular wedge 418 is resisted by the respective engagement surfaces 484, 488 of the teeth 438, 452. As illustrated in FIG. 51 any forward movement of the plunger 480 results in the beveled surface of the conical portion 432 cooperating with the complementary and corresponding beveled inner surface 454 of the annular wedge 418 and driving the annular wedge 418 to secure contact between the respective engagement surfaces 484, 488 and maintain the position of the annular wedge 418. Since the annular wedge 418 remains stationary, the plunger 408 cannot move outwardly in the body 404 because of the wedge-lock action occurring between the respective beveled surfaces 432, 440. The present invention provides a mechanism that allows movement in one direction only. While both the annular wedge 418 and the plunger 408 are shown with a taper or beveled surface, a further embodiment of the present invention may include an annular groove in the outer surface of the plunger and an annular expansion ring. Further, an alternative embodiment may have other configurations on the respective outer surface 436 of the annular wedge 418 and inner surface 454 of the socket 412; for example, a roughened or knurled surface.

Accordingly, the retaining pins 416 and groove or channels 428 cooperate to define the overall length of travel of the plunger 408 with respect to the cylindrical body 404; however, the annular wedge 418 cooperates with the cylindrical body 404 to limit the travel of the plunger in one direction only thus the bone screw 400 is collapsible only. Finally, the spring generates a predetermined amount of force, based upon the spring constant (K), resisting compression and depending upon the particular use or environment the amount of plunger travel and strength of the spring can be modified accordingly.

FIGS. 36 and 37 also illustrate an additional embodiment of a detent assembly, seen generally at 512, used to secure the bone screw 400 to a bone nail 16. As set forth with the previous embodiment, the detent member 512 engages the bone nail 16 and maintains a positional relationship between the body 404 of the bone screw 400 and the bone nail 16. Thus, the detent member 512 keeps the body 404 of the bone screw 400 in place while the plunger assembly 406 allows movement of the plunger 408 independent of the body 404 of the bone screw 400. As with the previous embodiment, the plunger assembly 406 moves to compensate for any compression or sliding between the femoral head 32 and femur 14. The detent assembly 512 is also suitable for use with a bone screw 400 that does not include a plunger assembly 406.

The detent assembly 512 generally includes an annular member shown herein as a lock ring 514; see FIGS. 55-57, having a plurality of slots or grooves 516 and a drive member, shown herein as a lock sleeve 518. The lock ring 514 further includes an inner surface 520 and an outer surface 522 along with respective first and second side surfaces 524, 526. As illustrated in FIG. 57 the respective first and second side surfaces 524, 526 are tapered or beveled surfaces 524a, 526a extending inwardly from the outer surface 522 toward the inner surface 520. As illustrated, the slots or grooves 516 extend inwardly, in an alternating manner, from the respective side surfaces 524, 526. As shown in FIGS. 55 to 57, a length of the slots 516 extending between the first and second side surfaces 524, 526 is less than a width of the lock ring 514 extending between the first and second side surfaces 524, 526. Additionally, as shown in FIG. 37, the body 504 has a length substantially parallel to a longitudinal axis, the lock ring 514 has a width substantially parallel to the longitudinal axis, and the width of the lock ring 514 is less than a length of said the body 504.

FIGS. 58-60 illustrate the lock sleeve 518 as a tubular member 528 having an outer surface 530 and an inner surface 532. The lock sleeve 518 further includes a first end and a second end 534, 536. The first end 534 including an outwardly extending tapered or beveled portion 538 and the second end 536 including a plurality of internal threads 540 and a head portion 542. The head portion 542 having a plurality of longitudinally extending slots or notches 544 extending inwardly from the second end 536. The head portion 542 may also include a shoulder 546 that engages the outer cortex 38 of the femur 14 whereby continued tightening or rotation of the bone screw 400 creates a force that draws the femoral head 32 toward the femur 14 and compresses the fracture 34.

FIG. 37 illustrates the lock ring 514 and lock sleeve 518 cooperating with the body 404 to form the detent assembly 512. As shown, the body 404 has a reduced diameter shaft portion 548 extending inwardly from the end 470 of the body 404 opposite the socket 412 to an outwardly beveled or tapered shoulder 550. A plurality of threads 552 are located on the end of the reduced diameter shaft portion 548 adjacent the end 470 of the body 404. A plurality of tabs 564 extend longitudinally outward from the end 470 of the body 404.

Figure 61:
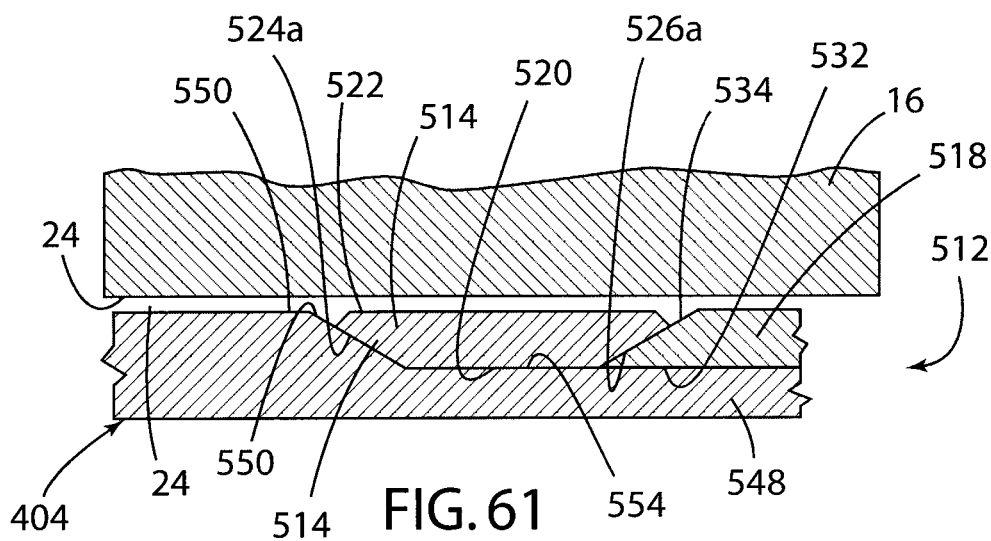
FIG. 61 is an enlarged cross-sectional schematic view illustrating the lock ring positioned flush with the outer surface of the body.
Figure 62:
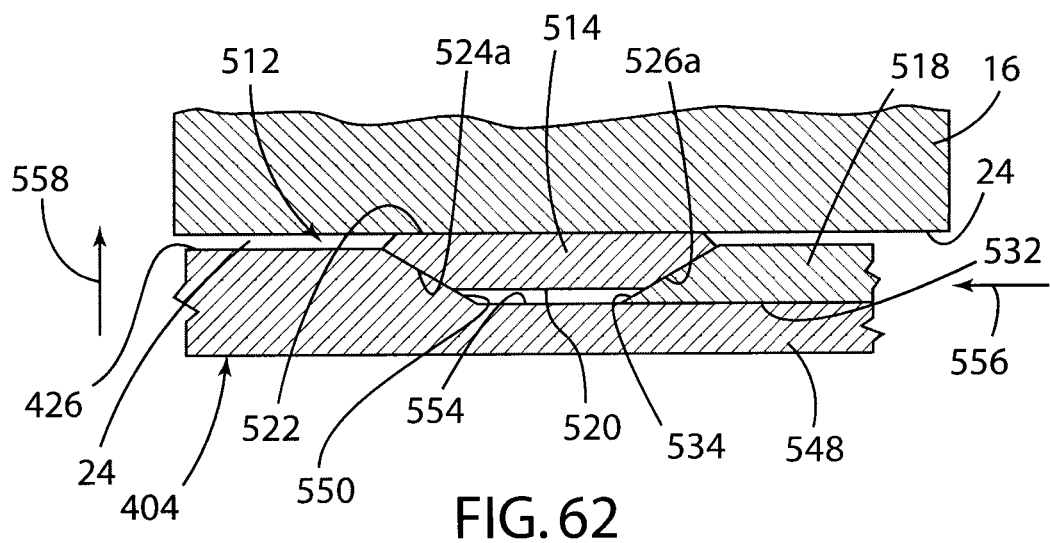
FIG. 62 is an enlarged cross-sectional schematic view illustrating the lock ring extending outwardly past the outer surface of the body.

FIGS. 61-62 illustrate operation of the detent assembly 512. Specifically, the lock ring 514 is placed on the shaft portion 548 of the body 504 with the inner surface 520 of the lock ring 514 placed adjacent the outer surface 554 of the shaft portion 548 such that the lock ring 514 is coaxial with the body 504. The first tapered side surface 524a of the lock ring 514 is placed adjacent the beveled or tapered shoulder 550 of the body 404. As illustrated, the outer surface 522 of the lock ring 514 is located at the same diameter or equal to the diameter of the outer circumferential surface 426 of the body 404. The inner surface 532 of the lock sleeve 518 having an inner diameter substantially the same as the outer diameter of the shaft portion 548. Accordingly, the lock sleeve 518 slides over the shaft portion 548 until the internal threads 540 of the lock sleeve 518 engage the outer threads 552 on the shaft portion 548. As illustrated in FIG. 61, the lock sleeve 518 is rotated until the beveled or tapered shoulder 550 engages the second tapered side surface 526a of the lock ring 514 and the respective outer diameters of the body 404, lock ring 514 and lock sleeve 518 are the same. Whereby, the bone screw 400 slides freely in the aperture 24 of the bone nail 16.

After the bone screw 400 is installed in the femoral head 32 and properly located, rotation of the lock sleeve 518 operates to drive the locking ring 514 radially outward, see FIG. 62 and into engagement with the aperture 24 on the bone nail 16. Specifically, as the lock sleeve 518 moves longitudinally in the direction illustrated by the arrow 556 the combination of beveled surfaces 538, 550 on the lock sleeve 518 and body 404 act on the complementary first and second beveled side surfaces 524a, 526a to urge the lock ring 514 radially outward in the direction of the arrow 558. When urged radially outward, the outer surface 522 of the lock ring 514 engages the inner surface of the aperture 24 in the bone nail 16 and creates a lock between the bone screw 400 and bone nail 16.

The slots or grooves 516 on the lock ring 514 operate to further secure and create a lot between the bone screw 400 and bone nail 16. The slots 516 are staggered or alternate between the respective first and second side surfaces 524, 526. When the lock ring 514 is urged radially outward the respective sides 560 of the slots 516 create an edge 562 that engages the inner surface of the aperture 24 to further lock the bone screw 400 in position on the bone nail 16. Primarily, the slots 516 provide additional means to resist rotation of the bone screw 400 with respect to the bone nail 16. In addition, the outer surface 522 of the lock ring 514 may have a roughened surface finish to assist in creating mechanical lock between the bone screw 400 and bone nail 16.

Once the lock sleeve 518 is rotated sufficiently to create a locking force between the lock ring 514 and aperture 24 of the bone nail 16 to secure the bone screw 400 to the bone nail 16, the tabs 564 can be bent over such that they engage the slots or notches 544 in the lock sleeve 518. Doing so prevents rotation of the lock sleeve 518 and maintains a lock between the bone screw 400 and bone nail 16.

Figure 63:
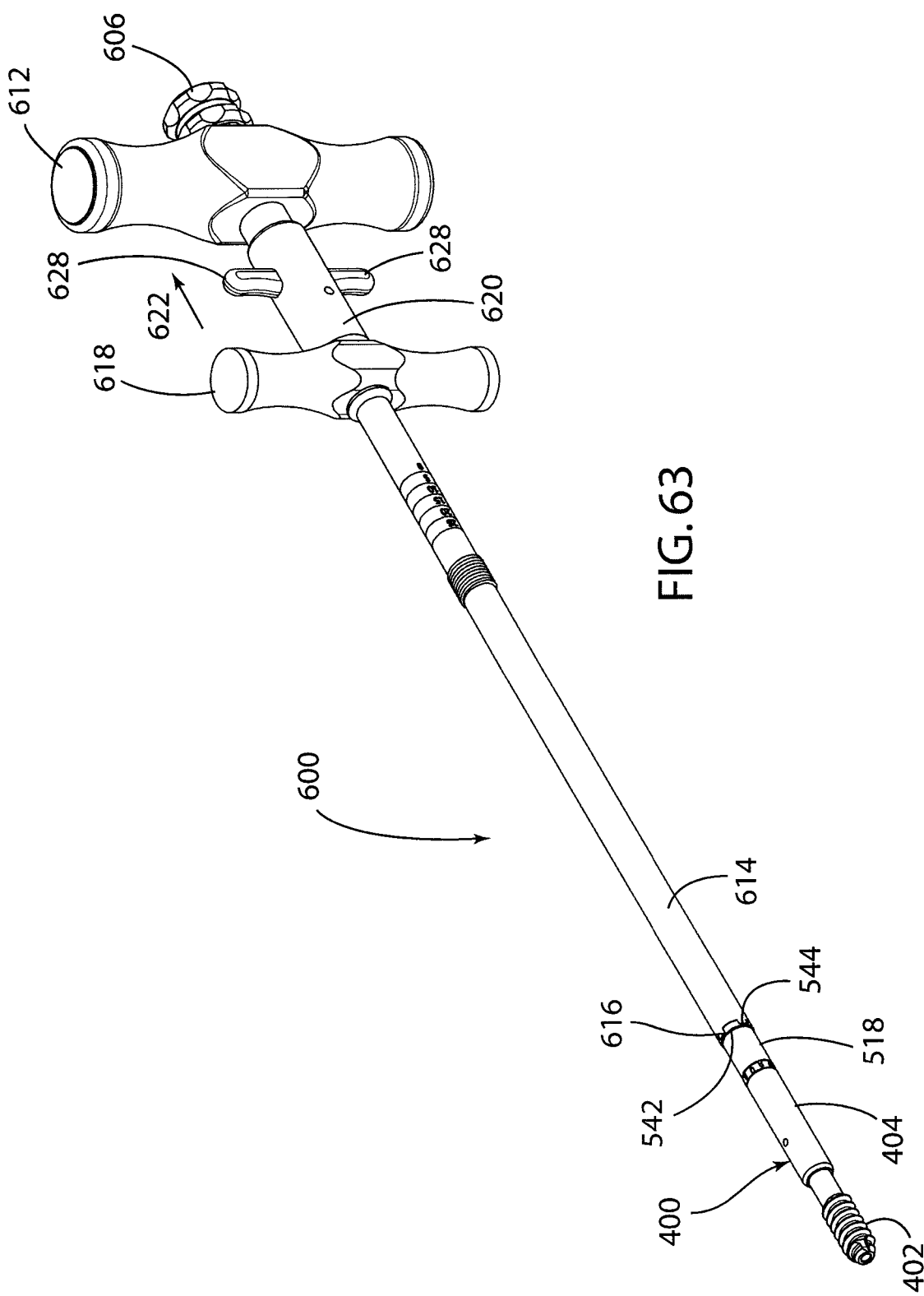
FIG. 63 is a perspective view of a second embodiment of installation equipment used for installing a bone screw according to the present invention.

FIGS. 63-65 illustrate a second embodiment of an installation tool, seen generally at 600, operative to engage the body 404 adjacent the end 470 of the bone screw 400. The installation tool 600 includes a first or inner member or capture rod 602. The capture rod 602 has a plurality of threads 604 on one end thereof. The threads 604 are complementary to and engage the plurality of threads 476 located in the end 470 of the bone screw 400. On the opposite end of the capture rod 602 is a knob 606 used to rotate the capture rod 602.

The installation tool 600 further includes a second or middle drive member or driver 608 disposed over the capture rod 602. As illustrated, the middle drive member 608 is a hollow rod or shaft having a hexagonal shaped drive portion 610 located on one end thereof. The hexagonal shaped drive portion 610 is complementary to and engages the internal drive socket 474. The middle drive member 608 includes a T-handle 612 spaced from the hexagonal shaped drive portion 610. The T-handle 612 is used to rotate the middle drive member 608.

The installation tool 600 also includes a third or outer drive member or driver 614. The outer drive member 614 is a hollow rod or shaft with both the middle drive member 608 and capture rod 602 disposed therein. The outer drive member 614 includes a plurality of axially extending engagement fingers 616 located on one end thereof. The engagement fingers 616 complementary to and adapted to engage the slots or notches 544 located in the head portion 542 of the lock sleeve 518. The outer drive member 614 also includes a T-handle 618 spaced from the engagement fingers 616. The T-handle 618 is used to rotate the outer drive member 614. Accordingly, as illustrated the inner member or capture rod 602, middle drive member 608 and outer drive member 614 are arranged in a nested relationship wherein each one rotates and moves axially independently of the others.

FIGS. 63-65 illustrates the engagement between the installation tool 600 and the bone screw 400. Specifically, the threads 604 of the capture rod 602 engage the threads 476 located in the end 470 of the bone screw 400 to attach the bone screw 400 to the installation tool 600. The inner drive member 608 slides over the inner member or capture rod 602 until the hexagonal shaped drive portion 610 engages the hexagonal shaped drive socket 474. Accordingly, rotation of the T-handle 612 of the inner drive member rotates the entire bone screw 400 such that the operator can properly insert the bone screw 400.

Once the bone screw 400 is placed in its proper position within the femoral head 32, the third or outer drive member is rotated using the T-handle 618 to turn or rotate the lock sleeve 518 wherein the internal threads 540 of the lock sleeve 518 that engage the outer threads 552 on the shaft portion 548 cause the lock sleeve 518 to move axially along the body 404 of the bone screw 400. Continued rotation of the lock sleeve 518 causes the beveled or tapered shoulder 550 of the lock sleeve 518, which engages the second tapered side surface 526a of the lock ring 514, to drive the locking ring 514 radially outward and into engagement with the aperture 24 on the bone nail 16.

The installation tool 600 further includes a latch mechanism 620 operative to engage or latch the outer drive member 614 to the second or inner drive member 608 such that they rotate together. Specifically, the outer drive member 614 rotates with the inner drive member 608 when the T-handle 612 of the inner drive member 608 is used to install the bone screw 400. After installation of the bone screw 400, the operator slides the latch mechanism 620 rearwardly, in the direction of the arrow 622, to disengage an end 624 of the latch mechanism 620 from a detent groove 626 located in the T-handle 618 of the outer drive member 614. As shown herein the latch mechanism 620 is slidably mounted to the inner drive member 608 such that it slides on but does not rotate about the inner drive member 608. In one embodiment thereof, the latch mechanism 620 can be biased, through a compression spring, into engagement with the T-handle 618 of the outer drive member 614. Accordingly, once the bone screw 400 is installed the operator pulls the latch mechanism 620 by grasping the arms 628 and pulling the latch mechanism 620 in the direction of the arrow 622 against the spring until the end 624 disengages from the detent groove 626. Once the latch mechanism 620 is disengaged, the T-handle 618 is used to rotate the outer drive member 614 and correspondingly the lock sleeve 518 to urge the lock ring 514 radially outward.

After the installation tool 600 and is removed, a lockout tube removal tool 630, see FIG. 66, is used to withdraw or remove the lock out tube 492. The lockout tube removal tool 630 has a left-hand threaded portion 632 that engages the left-hand threads 510 located in the head 502 of the lockout tube 492. Using the handle 636 the lockout tube removal tool 630 is rotated until the shoulder 634 fully engages the threads 502 of the lockout tube 492. Since the respective threads of the lockout tube 492 and removal tool 630 are left-handed continued rotation of the lockout tube removal tool 630 causes the lockout tube 492 to rotate, since the threads 506 on the outer surface 508 are right-handed, and ultimately be removed from the bone screw 400 through the second socket or passageway 468. Once the lockout tube 492 is removed the bone screw 400 may collapse as set forth herein.

While the installation tool 600 includes an outer drive member 614 operative to engage and rotate the lock sleeve 518, as set forth above, a bone screw 400 according to the present invention may not utilize the specific detent assembly 512 including the lock ring 514. In that event, the installation tool may be modified. Further, to the extent that the bone screw 400 does not include a plunger assembly 406 then the lockout tube 492 and lockout tube removal tool 630 would not be necessary.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus for repairing a bone fracture comprising:
 a bone screw including a body; and
 a detent assembly including an annular member having an inner surface, an annular member outer surface, a first side surface, and a second side surface, wherein said annular member has an opening extending between said first side surface and said second side surface, said annular member is coaxial with said body, and said first side surface and said second side surface of said annular member are beveled surfaces;
 said body having a shaft portion and a body outer surface, wherein said annular member surrounds said shaft portion with said inner surface of said annular member facing said shaft portion, wherein said annular member is movable between a first position and a second position, wherein positioning said annular member in said second position operates to secure said body from movement relative to a bone nail, and when said annular member is in said first position, said annular member outer surface of said annular member has an annular member diameter substantially equal to a body diameter of said body outer surface of said bone nail.

2. The apparatus as set forth in claim 1 including a drive member operative to engage said annular member and move said annular member towards said second position.

3. The apparatus as set forth in claim 2 wherein said drive member includes a threaded portion.

4. The apparatus as set forth in claim 1 wherein said annular member outer surface of said annular member engages the bone nail, and said annular member outer surface is configured to increase a holding force and correspondingly reduce movement of said body with respect to the bone nail.

5. An apparatus as set forth in claim 1 wherein said annular member includes a plurality of slots and a width extending between said first side surface and said second side surface, and said plurality of slots each have a length substantially parallel to a longitudinal axis of said apparatus and extend inwardly from one of said first and second side surfaces towards the other one of said first and second side surfaces, and said length of each of said plurality of slots is less than said width of said annular member.

6. The apparatus as set forth in claim 1 wherein said annular member includes a plurality of slots that alternate inwardly from one of said first and second side surfaces to the other one of said first and second side surfaces.

7. The apparatus as set forth in claim 1 including a drive member having a first end, wherein said body has a shoulder, and said first side surface of said annular member is adjacent to said shoulder of said body of said bone screw, said second side surface of said annular member is adjacent to said first end of said drive member, and said drive member is operative to engage said annular member and move said annular member towards said second position.

8. The apparatus as set forth in claim 1 wherein said annular member contacts said body outer surface of said body.

9. The apparatus as set forth in claim 1 wherein said body has a length substantially parallel to a longitudinal axis of said apparatus, and said annular member has a width substantially parallel to said longitudinal axis of said apparatus, and said width of said annular member is less than said length of said body.

10. The apparatus as recited in claim 1 wherein when said annular member is in said first position, said annular member outer surface of said annular member has an annular member diameter substantially equal to a body diameter of said body outer surface of said body.

11. An apparatus for repairing a bone fracture comprising:
a body including a body threaded portion, a body outer surface, and a body diameter;
a detent assembly on said body, said detent assembly including an annular member on and surrounding said body, said annular member having an inner surface, an annular member outer surface, a first side surface, a second side surface, an annular member diameter, and an opening extending between said first side surface and said second side surface, wherein said annular member is movable between a first position and a second position, wherein when said annular member is in said first position said annular member diameter of said annular member outer surface of said annular member is substantially equal to said body diameter of said body outer surface of said body, and when said annular member is in said second position, said annular member secures said body from movement relative to a bone nail, and at least a portion of said annular member extends radially outwardly from and past said body outer surface of said body; and
a drive member operative to engage said annular member and move said annular member towards said second position, wherein said drive member includes a drive threaded portion that engages said body threaded portion of said body, and rotation of said drive member moves said annular member towards said second position.

12. An apparatus for repairing a bone fracture comprising:
a body including a body threaded portion, a body outer surface, and a body diameter;
a detent assembly on said body, said detent assembly including an annular member on and surrounding said body, said annular member having an inner surface, an annular member outer surface, a first side surface, a second side surface, an annular member diameter, and an opening extending between said first side surface and said second side surface, wherein said annular member is movable between a first position and a second position, wherein when said annular member is in said first position said annular member diameter of said annular member outer surface of said annular member is substantially equal to said body diameter of said body outer surface of said body, and when said annular member is in said second position, said annular member secures said body from movement relative to a bone nail and at least a portion of said annular member extends radially outwardly from and past said annular member outer surface of said body; and
a drive member operative to engage said annular member and move said annular member towards said second position, wherein said drive member includes a drive threaded portion that engages said body threaded portion of said body, and rotation of said drive member moves said annular member towards said second position.

13. An apparatus for repairing a bone fracture comprising:
a body having a body outer surface; and
an annular member on said body, said annular member having an inner surface, an annular member outer surface, a first side surface, a second side surface, and an indentation extending inwardly from said annular member outer surface, wherein said annular member contacts said body outer surface of said body,
wherein said annular member is movable between a first position and a second position, and when said annular member is in said second position, said annular member moves radially outwardly to secure said body from movement relative to a bone nail.

14. The apparatus as set forth in claim 13 wherein said indentation of said annular member includes a plurality of alternating slots, and each of said plurality of alternating slots extend inwardly from one of said first side surface and said second side surface of said annular member.

15. The apparatus as set forth in claim 13 wherein said indentation of said annular member includes an edge.

16. The apparatus as set forth in claim 13 wherein when said annular member is in said second position, at least a portion of said annular member extends radially outwardly and past said body outer surface of said body.

17. The apparatus as recited in claim 13 wherein said annular member has an annular member diameter and said body has a body diameter, and when said annular member is in said first position, said annular member diameter of said outer surface of said annular member is substantially equal to said body diameter of a portion of said outer surface of said body, and when said annular member in in said second position, said annular member diameter of said annular member outer surface of said annular member is greater than said body diameter of said portion of said outer surface of said body to secure said body from movement relative to a bone nail.

* * * * *